US012629136B2

(12) United States Patent
Pourtahmasi Roshandeh et al.

(10) Patent No.: US 12,629,136 B2
(45) Date of Patent: *May 19, 2026

(54) METHOD AND SYSTEM FOR GENERATING A THREE- DIMENSIONAL ULTRASOUND IMAGE OF A TISSUE VOLUME

(71) Applicant: Exo Imaging, Inc., Santa Clara, CA (US)

(72) Inventors: Koosha Pourtahmasi Roshandeh, Alberta (CA); Dornoosh Zonoobi, Edmonton (CA); Abhilash Rakkunedeth, Alberta (CA); Masood Dehghan, Alberta (CA); Jacob Jaremko, Alberta (CA)

(73) Assignee: Exo Imaging, Inc., Santa Clara, CA (US)

( * ) Notice: Subject to any disclaimer, the term of this patent is extended or adjusted under 35 U.S.C. 154(b) by 69 days.

This patent is subject to a terminal disclaimer.

(21) Appl. No.: 18/609,965

(22) Filed: Mar. 19, 2024

(65) Prior Publication Data

US 2024/0252148 A1     Aug. 1, 2024

Related U.S. Application Data

(63) Continuation of application No. 18/460,158, filed on Sep. 1, 2023, now Pat. No. 12,329,581, which is a
(Continued)

(30) Foreign Application Priority Data

Nov. 19, 2018    (SG) ........................... 10201810322Y

(51) Int. Cl.
| | |
|---|---|
| *A61B 8/00* | (2006.01) |
| *G01S 15/89* | (2006.01) |
| *G06N 3/02* | (2006.01) |

(52) U.S. Cl.
CPC ........... *A61B 8/483* (2013.01); *A61B 8/5207* (2013.01); *G01S 15/8915* (2013.01); *G01S 15/8993* (2013.01); *G06N 3/02* (2013.01)

(58) Field of Classification Search
CPC . A61B 5/7624; A61B 5/7267; G01N 29/4481
See application file for complete search history.

(56) References Cited

U.S. PATENT DOCUMENTS

| | | |
|---|---|---|
| 5,582,173 A | 12/1996 | Li |
| 6,012,458 A | 1/2000 | Mo et al. |

(Continued)

FOREIGN PATENT DOCUMENTS

| | | |
|---|---|---|
| CN | 108171694 A | 6/2018 |

OTHER PUBLICATIONS

R. Prevost et al, "3D freehand ultrasound without external tracking using deep learning", Medical Image Analysis, vol. 48, pp. 187-202, Jun. 2018 (Year: 2018).*
(Continued)

*Primary Examiner* — Nyrobi Celestine
(74) *Attorney, Agent, or Firm* — Morgan, Lewis & Bockius LLP

(57) ABSTRACT

A method includes generating a series of two-dimensional (2D) ultrasound images of a tissue volume associated with a plurality of positions, respectively, along a scanning direction of the tissue volume. The method includes, for a pair of consecutive 2D ultrasound images, using a deep neural network to classify a difference between the pair of consecutive 2D ultrasound images of the series of 2D ultrasound images. The deep neural network is trained to classify differences between images based on one of a plurality of predefined classes. The method includes modifying a number of 2D ultrasound images in the series of 2D ultrasound images based on the classification of the difference between
(Continued)

Slice n  Slice n+1          Difference Image          Distance Predictor Network the pair of consecutive 2D ultrasound images of the series of 2D ultrasound images, thereby producing a modified series of 2D ultrasound images. The method includes performing a measurement of tissue using the modified series of 2D ultrasound images.

20 Claims, 10 Drawing Sheets

Related U.S. Application Data continuation of application No. 17/294,689, filed as application No. PCT/SG2019/050564 on Nov. 19, 2019, now Pat. No. 11,779,309.

(56) References Cited

U.S. PATENT DOCUMENTS

| | | | |
|---|---|---|---|
| 11,779,309 | B2 | 10/2023 | Pourtahmasi Roshandeh et al. |
| 2015/0366535 | A1 | 12/2015 | Eggers et al. |
| 2017/0367685 | A1 | 12/2017 | Zou et al. |
| 2018/0260997 | A1 | 9/2018 | Petkov et al. |
| 2024/0041432 | A1 | 2/2024 | Pourtahmasi Roshandeh et al. |

OTHER PUBLICATIONS

MEDO DX PTE. Ltd., PCT/SG2019/050564, International Search Report and Written Opinion, Feb. 3, 2020, 11 pgs.

MEDO DX PTE. Ltd., PCT/SG2019/050564, International Preliminary Report on Patentability, May 25, 2021, 7 pgs.

Tang, Yuan, "TF. Learn: TensorFlow's High-level Module for Distributed Machine Learning", arXiv, Dec. 2016, 'ages 1-7, 1612.04251v1.

Simonyan, Karen et al., "Very Deep Convolutional Networks for Large-scale Image Recognition", arXiv, Apr. 2015, 'ages 1-14, 1409.1556.

Prevost, R. et al., "3D freehand ultrasound without external tracking using deep learning", Medical Image Analysis, okugust, 2018, pp. 187-202, vol. 48, Elsevier.

Laporte, Catherine et al., "Learning to estimate out-of-plane motion in ultrasound imagery of real tissue", Medical mage Analysis, Apr. 2011, 12 Pages, vol. 15, Issue 2, Elsevier.

Pourtahmasi Roshandeh et al., Non-Final Office Action, U.S. Appl. No. 17/294,689, Apr. 18, 2023, 18 pgs.

Pourtahmasi Roshandeh et al., Notice of Allowance, U.S. Appl. No. 17/294,689, Aug. 23, 2023, 9 pgs.

Pourtahmasi Roshandeh et al., Non-Final Office Action, U.S. Appl. No. 18/460,158, Oct. 25, 2024, 8 pgs.

\* cited by examiner

100

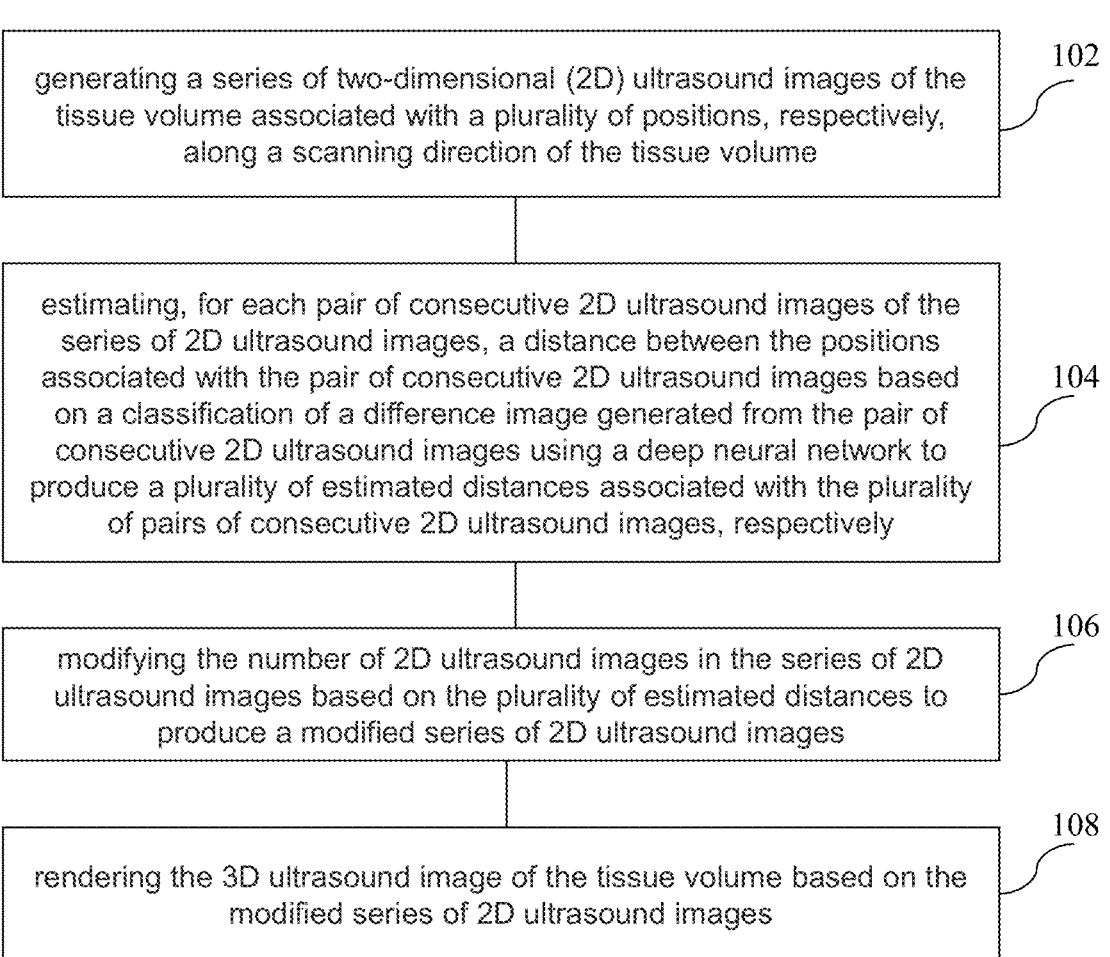

generating a series of two-dimensional (2D) ultrasound images of the tissue volume associated with a plurality of positions, respectively, along a scanning direction of the tissue volume                    102 estimating, for each pair of consecutive 2D ultrasound images of the series of 2D ultrasound images, a distance between the positions associated with the pair of consecutive 2D ultrasound images based on a classification of a difference image generated from the pair of consecutive 2D ultrasound images using a deep neural network to produce a plurality of estimated distances associated with the plurality of pairs of consecutive 2D ultrasound images, respectively                    104 modifying the number of 2D ultrasound images in the series of 2D ultrasound images based on the plurality of estimated distances to produce a modified series of 2D ultrasound images                    106 rendering the 3D ultrasound image of the tissue volume based on the modified series of 2D ultrasound images                    108

FIG. 1

METHOD AND SYSTEM FOR GENERATING A THREE- DIMENSIONAL ULTRASOUND IMAGE OF A TISSUE VOLUME

RELATED APPLICATIONS

This application is a continuation of U.S. patent application Ser. No. 18/460,158, filed on Sep. 1, 2023, which is a continuation of U.S. patent application Ser. No. 17/294,689, filed on May 18, 2021, which is a national stage entry according to 35 U.S.C. § 371 of PCT Application No. PCT/SG2019/050564, filed on Nov. 19, 2019; which claims priority to Singapore Patent Application Serial No. 10201810322Y, filed on Nov. 19, 2018; each of which is incorporated herein by reference in its entirety.

TECHNICAL FIELD

The present invention generally relates to a method and a system for generating a three-dimensional (3D) ultrasound image of a tissue volume, and more particularly, with respect to a freehand ultrasound scanning of the tissue volume.

BACKGROUND

Two-dimensional (2D) ultrasound (US) imaging is safe, inexpensive and widely used in medical practices, as well as having real-time and high resolution capabilities. Conventional 2D ultrasound imaging techniques may be configured to extract a 2D ultrasound image (which may also be referred to as a cross-sectional image, an image plane/frame or a B-mode/B-scan image) of the tissue volume scanned by an ultrasound probe. However, various conventional 2D ultrasound imaging techniques have the inherent limitation of relying upon a 2D ultrasound image to represent a 3D tissue volume. For example, an anatomical structure such as bone cannot be completely visualized in 2D dimensions. The ultrasound probe may be manually operated (moved) by an operator to obtain a 2D ultrasound image (or a series of 2D ultrasound images) of the tissue volume (e.g., a body organ). These ultrasound images may then be mentally visualised by an operator (e.g., a radiologist) to form a subjective impression of the 3D anatomy and pathology. However, such conventional techniques are time-consuming, inefficient and inaccurate, which leads to outcome variability and incorrect diagnosis.

For example, as the operator is required to know how to properly position the ultrasound probe on the subject to capture a medically relevant 2D ultrasound image of an anatomical structure, an inexperienced operator may have considerable difficulties capturing medically relevant ultrasound images of the anatomical structure. Moreover, such conventional 2D ultrasound imaging techniques may be suboptimal for monitoring therapeutic procedures and follow-up examinations, as they only provide a limited sample of the 3D anatomical structure obtained at one or more arbitrary locations. Furthermore, at follow-up examinations, it is often difficult to ensure that the ultrasound probe is positioned to capture a 2D ultrasound image of an anatomical structure at the same image plane (same position) with the same orientation as a previous 2D ultrasound image captured at a previous examination. Therefore, such conventional 2D ultrasound imaging techniques may further suffer from lack of repeatability/consistency.

On the other hand, various conventional 3D ultrasound imaging techniques acquire the whole 3D anatomy, instead of one or more 2D ultrasound images, and attract growing interest from researchers/clinicians as they extend the narrow field-of-view of conventional 2D ultrasound imaging to allow better illustration of complex anatomy structures and provide repeatable and precise volume analysis. With a 3D volume data set, operators are able to perform volume rendering, 3D image segmentation and measurement on the 3D anatomy to extract useful diagnostic information.

Over the past few decades, researchers have proposed various 3D ultrasound imaging techniques for the construction and visualization of 3D ultrasound volume. These conventional 3D ultrasound imaging techniques may generally be divided into two main categories, namely, direct 3D ultrasound scanning using a 3D ultrasound probe and 3D image reconstruction from 2D ultrasound scanning (freehand scanning) using a 2D ultrasound probe.

Currently, commonly used commercial 3D ultrasound probes are based on mechanical scanning or electronic beam steering. In mechanical scanning, an ultrasound transducer array and a stepper motor may be integrated into a dedicated housing of the ultrasound probe, which allows fast acquisition of a 3D ultrasound volume. In electronic beam steering, the excitation of individual elements in the transducer array may be timed such that the ultrasound waves sweep over the entire 3D volume. However, the drawbacks of such conventional 3D ultrasound probes are that, in general, they are relatively bulky and expensive, as well as being only able to cover a limited field of view due to the physical size of the ultrasound transducer.

In 3D image reconstruction from 2D ultrasound scanning (freehand scanning), a conventional 2D ultrasound probe may be moved by hand in a desired manner to scan a tissue volume. For example, the operator may adjust the pace of the ultrasound probe's scanning motion to control the number of 2D ultrasound images acquired of the tissue volume, and thus, control the resolution of the 3D volumetric data rendered from such 2D ultrasound images acquired. In such a freehand scanning approach, there generally exist two categories, namely, freehand scanning with position tracking (requires tracking hardware such as a position sensor) to provide location information of the ultrasound probe and free hand scanning without position tracking.

In the freehand scanning with position tracking approach, a position sensor (e.g., a magnetic field sensor or an optical sensor) may be rigidly attached to the ultrasound probe. However, performing freehand scanning with a position sensor has a number of drawbacks, including non-trivial and time consuming end-user calibrations when the location of the position sensor on (with respect to) the ultrasound probe changes and cumbersome constraints on the scanning protocol. For example, the operator must be careful not to stray outside the operating region of the position sensor, and must consider the limitations of the sensor during scanning, e.g., keeping a magnetic field sensor away from electro-magnetic interference, or keeping an optical sensor along a clear line of sight from the ultrasound probe to sensor. Accordingly, one of the main obstacles to practical applications of the freehand scanning with position tracking approach is the drawbacks associated with the position sensor itself.

In the freehand scanning without position tracking approach (which may also be referred to as a sensorless freehand scanning approach), patterns of noise within the ultrasound images can be decoded to estimate the distance between images. Conventional speckle decorrelation techniques have been disclosed for performing freehand 3D ultrasound imaging without requiring position tracking. In particular, conventional speckle decorrelation techniques are configured to estimate the relative position and orientation between a pair of consecutive 2D ultrasound images based on image speckle decorrelation between these images. However, such techniques assume that there is a continuity in the speckle pattern which requires fully developed speckle areas. The pattern of noise between images may not show enough continuity to allow use of such techniques, especially when access to raw data is restricted. Moreover, since the acquired ultrasound images are based on the superposition of several phenomena, the assumed mathematical model may not be valid in practice, which results in poor estimation/accuracy.

A need therefore exists to provide a method and a system for generating a 3D ultrasound image of a tissue volume (e.g., including one or more internal anatomical structures) that seek to overcome, or at least ameliorate, one or more of the deficiencies associated with conventional methods and systems, and in particular, with respect to a freehand ultrasound scanning of the tissue volume.

SUMMARY

According to a first aspect, there is provided a method for generating a three-dimensional (3D) ultrasound image of a tissue volume using at least one processor, the method comprising:

generating a series of two-dimensional (2D) ultrasound images of the tissue volume associated with a plurality of positions, respectively, along a scanning direction of the tissue volume;

estimating, for each pair of consecutive 2D ultrasound images of the series of 2D ultrasound images, a distance between the positions associated with the pair of consecutive 2D ultrasound images based on a classification of a difference image generated from the pair of consecutive 2D ultrasound images using a deep neural network to produce a plurality of estimated distances associated with the plurality of pairs of consecutive 2D ultrasound images, respectively;

modifying the number of 2D ultrasound images in the series of 2D ultrasound images based on the plurality of estimated distances to produce a modified series of 2D ultrasound images; and rendering the 3D ultrasound image of the tissue volume based on the modified series of 2D ultrasound images.

In various embodiments, the deep neural network is trained to classify the difference image into one of a plurality of classes, the plurality of classes corresponding to a plurality of distance values, respectively; and said distance is estimated to be the distance value corresponding to the class in which the difference image is classified into.

In various embodiments, the difference image comprises pixels, each pixel having a difference pixel value determined based on a difference between pixel values of corresponding pixels of the pair of consecutive 2D ultrasound images.

In various embodiments, the above-mentioned modifying the number of 2D ultrasound images comprises removing each 2D ultrasound image of the series of 2D ultrasound images that satisfies a predetermined image removal condition; and inserting one or more additional 2D ultrasound images in between each pair of consecutive 2D ultrasound images that satisfies a predetermined image insertion condition.

In various embodiments, the one or more additional 2D ultrasound images are each generated based on an interpolation of the pair of consecutive 2D ultrasound images in between which the one or more additional 2D ultrasound images are to be inserted.

In various embodiments, the plurality of distance values of the plurality of classes, respectively, do not overlap and are each configured based on a scan resolution.

In various embodiments, each of the plurality of distance values is configured as a multiple of the scan resolution; the predetermined image removal condition for removing a 2D ultrasound image is based on whether the estimated distance associated with a first pair of consecutive 2D ultrasound images including the 2D ultrasound image is equal to a predefined multiple of the scan resolution, and the predetermined image insertion condition for inserting one or more additional 2D ultrasound images in between a pair of consecutive 2D ultrasound images is based on whether the estimated distance associated with the pair of consecutive 2D ultrasound images is greater than the predefined multiple of the scan resolution.

In various embodiments, the predetermined image removal condition is further based on whether the estimated distance associated with a second pair of consecutive 2D ultrasound images including the 2D ultrasound image is equal to the predefined multiple of the scan resolution, whereby if the estimated distances associated with the first pair and the second pair are both equal to the predefined multiple of the scan resolution, a second distance between the positions associated with the other 2D ultrasound image of the first pair and the other 2D ultrasound image of the second pair is estimated based on a classification of a second difference image generated from the other 2D ultrasound image of the first pair and the other 2D ultrasound image of the second pair using the deep neural network, and the predetermined image removal condition is further based on whether the second estimated distance is equal to the predefined multiple of the scan resolution.

In various embodiments, the number of additional 2D ultrasound images generated is based on the number of times the estimated distance is a multiple of the scan resolution.

In various embodiments, the predefined multiple of the scan resolution is one.

According to a second aspect, there is provided a system for generating a three-dimensional (3D) ultrasound image of a tissue volume, the system comprising:

an ultrasound transducer;

a memory; and at least one processor communicatively coupled to the memory and the ultrasound transducer, and configured to:

generate a series of two-dimensional (2D) ultrasound images of the tissue volume associated with a plurality of positions, respectively, along a scanning direction of the tissue volume based on a series of ultrasound waves acquired by the ultrasound transducer at the plurality of positions;

estimate, for each pair of consecutive 2D ultrasound images of the series of 2D ultrasound images, a distance between the positions associated with the pair of consecutive 2D ultrasound images based on a classification of a difference image generated from the pair of consecutive 2D ultrasound images using a deep neural network to produce a plurality of estimated distances associated with the plurality of pairs of consecutive 2D ultrasound images, respectively;

modify the number of 2D ultrasound images in the series of 2D ultrasound images based on the plurality of estimated distances to produce a modified set of 2D ultrasound images; and render the 3D ultrasound image of the tissue volume based on the modified series of 2D ultrasound images.

In various embodiments, the deep neural network is trained to classify the difference image into one of a plurality of classes, the plurality of classes corresponding to a plurality of distance values, respectively; and said distance is estimated to be the distance value corresponding to the class in which the difference image is classified into.

In various embodiments, the difference image comprises pixels, each pixel having a difference pixel value determined based on a difference between pixel values of corresponding pixels of the pair of consecutive 2D ultrasound images.

In various embodiments, the above-mentioned modify the number of 2D ultrasound images comprises removing each 2D ultrasound image of the series of 2D ultrasound images that satisfies a predetermined image removal condition; and inserting one or more additional 2D ultrasound images in between each pair of consecutive 2D ultrasound images that satisfies a predetermined image insertion condition.

In various embodiments, the one or more additional 2D ultrasound images are each generated based on an interpolation of the pair of consecutive 2D ultrasound images in between which the one or more additional 2D ultrasound images are to be inserted.

In various embodiments, the plurality of distance values of the plurality of classes, respectively, do not overlap and are each configured based on a scan resolution.

In various embodiments, each of the plurality of distance values is configured as a multiple of the scan resolution, the predetermined image removal condition for removing a 2D ultrasound image is based on whether the estimated distance associated with a first pair of consecutive 2D ultrasound images including the 2D ultrasound image is equal to a predefined multiple of the scan resolution, and the predetermined image insertion condition for inserting one or more additional 2D ultrasound images in between a pair of consecutive 2D ultrasound images is based on whether the estimated distance associated with the pair of consecutive 2D ultrasound images is greater than the predefined multiple of the scan resolution.

In various embodiments, the predetermined image removal condition is further based on whether the estimated distance associated with a second pair of consecutive 2D ultrasound images including the 2D ultrasound image is equal to the predefined multiple of the scan resolution, whereby if the estimated distances associated with the first pair and the second pair are both equal to the predefined multiple of the scan resolution, a second distance between the positions associated with the other 2D ultrasound image of the first pair and the other 2D ultrasound image of the second pair is estimated based on a classification of a second difference image generated from the other 2D ultrasound image of the first pair and the other 2D ultrasound image of the second pair using the deep neural network, and the predetermined image removal condition is further based on whether the second estimated distance is equal to the predefined multiple of the scan resolution.

In various embodiments, the number of additional 2D ultrasound images generated is based on the number of times the estimated distance is a multiple of the scan resolution.

In various embodiments, the predefined multiple of the scan resolution is one.

In various embodiments, the ultrasound transducer is installed in a freehand ultrasound probe.

According to a third aspect, there is provided a computer program product, embodied in one or more non-transitory computer-readable storage mediums, comprising instructions executable by at least one processor to perform a method for generating a three-dimensional (3D) ultrasound image of a tissue volume, the method comprising:

generating a series of two-dimensional (2D) ultrasound images of the tissue volume associated with a plurality of positions, respectively, along a scanning direction of the tissue volume;

estimating, for each pair of consecutive 2D ultrasound images of the series of 2D ultrasound images, a distance between the positions associated with the pair of consecutive 2D ultrasound images based on a classification of a difference image generated from the pair of consecutive 2D ultrasound images using a deep neural network to produce a plurality of estimated distances associated with the plurality of pairs of consecutive 2D ultrasound images, respectively;

modifying the number of 2D ultrasound images in the series of 2D ultrasound images based on the plurality of estimated distances to produce a modified set of 2D ultrasound images; and rendering the 3D ultrasound image of the tissue volume based on the modified series of 2D ultrasound images.

BRIEF DESCRIPTION OF THE DRAWINGS

The non-limiting embodiments will be better understood and readily apparent to one of the ordinary skill in the art from the following written description, by way of example only, and in conjunction with the drawings, in which:

FIG. 1 depicts a schematic flow diagram of a method for generating a 3D ultrasound image of a tissue volume according to various embodiments;

DETAILED DESCRIPTION

Figure 2:
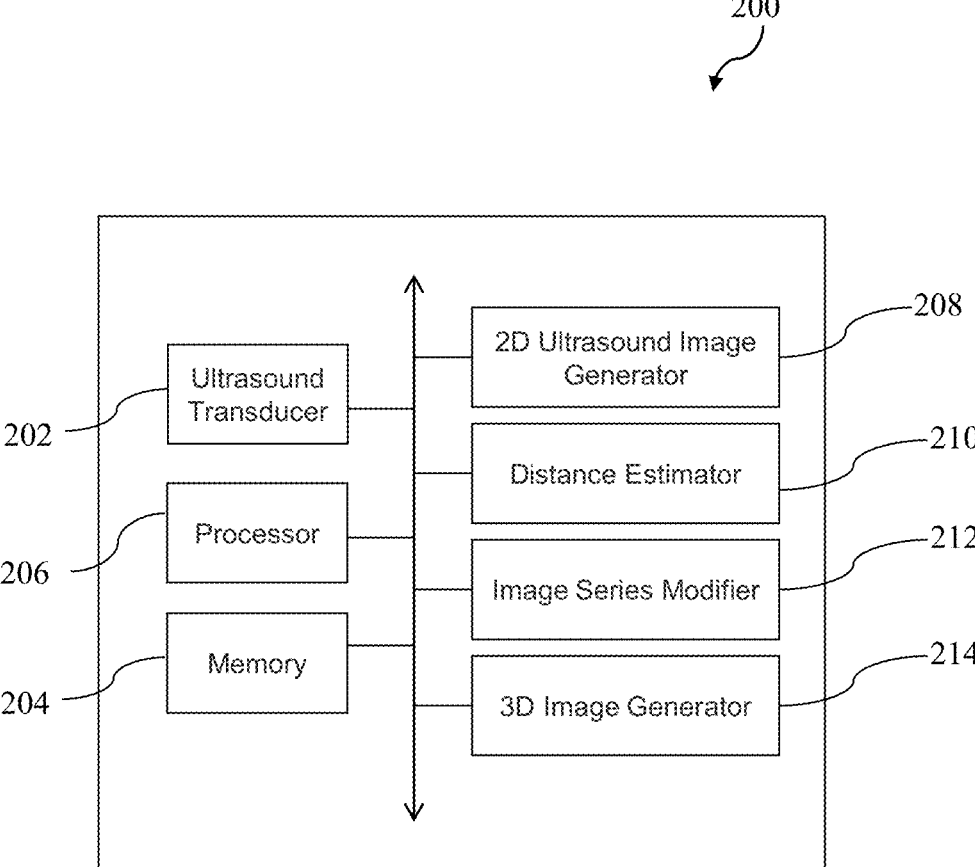
FIG. 2 depicts a schematic block diagram of a system for generating a 3D ultrasound image of a tissue volume according to various embodiments, such as corresponding to the method as depicted in FIG. 1.

Various embodiments provide a method (computer-implemented method) and a system including a memory and at least one processor communicatively coupled to the memory) for generating a three-dimensional (3D) ultrasound image of a tissue volume (e.g., including one or more internal anatomical structures), and more particularly, with respect to a freehand ultrasound scanning of the tissue volume using an ultrasound probe or transducer (e.g., an ultrasound probe or transducer configured to capture a series of two-dimensional (2D) ultrasound images associated with a plurality of positions along a scanning direction, which may herein be simply referred to as a 2D ultrasound probe or transducer). For example, the internal anatomical structure may be an organ of the human or animal body, such as but not limited to, any one or more of hip-bone, elbow, carotid artery, heart, lung(s), stomach, liver, and kidney(s).

As mentioned in the background, 2D ultrasound imaging is safe and inexpensive. However, acquiring a number of 2D ultrasound images and then mentally visualizing them to form a subjective impression of the 3D anatomy and pathology may be time consuming, inefficient and inaccurate, leading to outcome variability and incorrect diagnosis. Therefore, it may be desirable to obtain a 3D ultrasound image of the tissue volume to allow a better depiction of the tissue volume (e.g., including one or more internal anatomical structures), as well as facilitating volume analysis such that accurate and useful diagnostic information may be obtained from the 3D ultrasound image. However, in general, conventional 3D ultrasound probes configured to perform direct 3D ultrasound scanning of a tissue volume are relatively bulky and expensive.

Accordingly, various embodiments provide a method and a system for generating a 3D ultrasound image of a tissue volume based on a series of 2D ultrasound images of the tissue volume acquired from scanning the tissue volume using a 2D ultrasound transducer, and more particularly, with respect to a freehand ultrasound scanning using a 2D ultrasound transducer. A 3D ultrasound image of the tissue volume may then be rendered based on the series of 2D ultrasound images (or more specifically, a modified series of 2D ultrasound images as will be described later according to various embodiments, to, for example, improve the image resolution in an axial dimension of the 3D ultrasound image rendered). Such an approach of rendering a 3D ultrasound image (3D ultrasound volume) advantageously reduces cost as it avoids the use of a relatively expensive 3D ultrasound probe to scan the tissue volume. Moreover, the 3D ultrasound images generated according to various embodiments have advantageously been found to be satisfactorily similar in quality to the 3D ultrasound images generated from conventional 3D ultrasound probes (i.e., direct 3D ultrasound scanning using a 3D ultrasound probe).

FIG. 1 depicts a schematic flow diagram of a method 100 (computer-implemented method) for generating a 3D ultrasound image of a tissue volume (including one or more internal anatomical structures) using at least one processor. The method 100 comprises a step 102 of generating a series (or sequence or set) of 2D ultrasound images (which may also be interchangeably referred to as a cross-sectional image, an image plane, an image frame/slice or a B-mode/B-scan image) of the tissue volume associated with a plurality of positions, respectively along a scanning direction of the tissue volume. In this regard, the series of 2D ultrasound images may be respectively generated based on a series of ultrasound waves acquired by an ultrasound transducer positioned at the plurality of positions with respect to a plurality of time instances. The method 100 further comprises a step 104 of estimating, for each pair of consecutive 2D ultrasound images (each pair of immediately adjacent or neighbouring 2D ultrasound images) of the series of 2D ultrasound images, a distance between the positions associated with the pair of consecutive 2D ultrasound images based on a classification of a difference image generated from the pair of consecutive 2D ultrasound images using a deep neural network to produce a plurality of estimated distances associated with the plurality of pairs of consecutive 2D ultrasound images, respectively; a step 106 of modifying the number of 2D ultrasound images in the series of 2D ultrasound images based on the plurality of estimated distances to produce a modified series of 2D ultrasound images; and a step 108 of rendering the 3D ultrasound image of tissue volume based on the modified series of 2D ultrasound images.

In various embodiments, in relation to step 102, an ultrasound transducer configured to emit ultrasound waves with respect to a plane (e.g., a cross-sectional plane perpendicular to the scanning direction) of a tissue volume and acquire the ultrasound waves reflected from such a plane of the tissue volume may be used to acquire a series of ultrasound waves (in time series) at a plurality of positions along a scanning direction of the tissue volume. Such an ultrasound transducer may be referred to as a 2D ultrasound transducer.

As mentioned hereinbefore, various embodiments are particularly directed to a freehand ultrasound scanning of the tissue volume. In this regard, a 2D ultrasound transducer (or a portable handheld ultrasound probe comprising a 2D ultrasound transducer) may be moved by an operator along a scanning direction of the tissue volume (e.g., across a length of the tissue volume along an axis) so as to perform ultrasound scanning of the tissue volume whereby a series of ultrasound waves are acquired by the 2D ultrasound transducer at a plurality of positions, respectively, along the scanning direction with respect to a plurality of time instances. The ultrasound waves received at each time instance (at the corresponding position) may then be processed to generate a 2D ultrasound image having associated therewith the corresponding position in a manner known in the art and thus need not be described herein in detail. Accordingly, a series of 2D ultrasound images of the tissue volume may be acquired, each 2D ultrasound image having an associated position (e.g., tagged or labelled with an associated position information), for example, corresponding to the position of the 2D ultrasound transducer at which the ultrasound waves (based on which the 2D ultrasound image is generated) were acquired or corresponding to the position/location along the tissue volume at which the ultrasound waves acquired by 2D ultrasound transducer were reflected from.

The 2D ultrasound transducer may be any conventional 2D ultrasound transducer configured to emit and acquire ultrasound waves with respect to a plane of a tissue volume and thus need not be described herein in detail. For example and without limitation, a conventional 2D ultrasound transducer may comprise an array of transducer elements configured to emit and acquire ultrasound waves with respect to a plane of a tissue volume. Therefore, it will be appreciated by a person skilled in the art that the present is not limited to any particular type of 2D ultrasound transducer.

In relation to step 104, for each pair of consecutive 2D ultrasound images of the plurality of 2D ultrasound images, a distance therebetween (which may also be referred to as a separation, a relative distance or a Euclidean distance) is estimated, that is, the distance between the positions associated with the pair of consecutive 2D ultrasound images is estimated. The distance may be along an axis parallel to the scanning direction, or along an axis perpendicular to the 2D ultrasound image. In particular, a difference image is generated from the pair of consecutive 2D ultrasound images, and the distance between the positions associated with the pair of consecutive 2D ultrasound images is estimated based on a classification of such a difference image using a deep neural network. In this manner, the distance between the two consecutive 2D ultrasound images can advantageously be estimated (or determined or predicted) without utilizing position tracking, which thus overcomes, or at least ameliorates, various deficiencies associated with conventional freehand scanning approaches that require position tracking. Furthermore, generating a difference image and then estimating the distance based on a classification of such a difference image using a deep neural network has been found to be able to produce a sufficiently accurate estimate of the actual distance (e.g., accurate to the resolution of the ultrasound transducer).

In various embodiments, in relation to step 106, the number of 2D ultrasound images in the series of 2D ultrasound images generated in step 102 is then modified based on the plurality of estimated distances. In various embodiments, consecutive 2D ultrasound images that are determined to be "too close" to each other (e.g., less than to a first predefined threshold, such as the resolution of the ultrasound transducer) may have an image thereof removed. In various embodiments, consecutive 2D ultrasound images that are determined to be "too far" apart (e.g., a second predefined threshold or greater, such as twice the resolution of the ultrasound transducer or greater) may have one or more additional 2D ultrasound images (e.g., each being interpolated from the two consecutive 2D ultrasound images) inserted therebetween. In this manner, for example, the modified series of 2D ultrasound images would advantageously be substantially evenly or regularly spaced apart (e.g., spaced apart by the resolution of the ultrasound transducer), which has been found to result in a significant improvement in the quality of the 3D ultrasound image of the tissue volume rendered in step 108 based on such a modified series of 2D ultrasound images.

In relation to step 108, various conventional 3D image rendering techniques for rendering a 3D image based on a series of 2D images are known in the art and thus need not be described herein. That is, it can be understood by a person skilled in the art that any 3D image rendering technique known in the art as desired or as appropriate may be applied in step 108 to render the 3D ultrasound image based on a series of 2D ultrasound images, and the non-limiting embodiments are not limited to any particular type of 3D image rendering technique or system.

In various embodiments, the deep neural network is trained to classify the difference image into one of a plurality of classes, the plurality of classes corresponding to a plurality of distance values, respectively. In this regard, the distance is estimated to be the distance value corresponding to the class in which the difference image is classified into. For example, the plurality of classes may correspond to a plurality of machine learning classifiers trained for classifying a difference image (as an input) into one of the plurality of classes, and thus, into the corresponding one of the distance values (as an output). In various embodiments, the deep neural network may be trained based on a training dataset (e.g., a training sample) comprising a plurality of labelled difference images, each labelled difference image being labelled (or tagged) with a predetermined one of a plurality of classes which the difference image belongs to. For example, each labelled difference image may be obtained by generating a difference image from two 2D ultrasound images obtained at a known distance apart, and then labelling the difference image generated with such a known distance to obtain the labelled difference image. In various embodiments, such a known distance may be specifically configured (or set) or predefined by acquiring the two 2D ultrasound images at the predefined distance apart, such as at a multiple of the resolution of the ultrasound transducer. For example, the above-mentioned two 2D ultrasound images may be obtained using a 2D ultrasound transducer by positioning the 2D ultrasound transducer at two positions apart corresponding to the predefined distance at two time instances or a 3D ultrasound transducer by extracting two 2D ultrasound images at two positions apart corresponding to the predefined distance from the 3D ultrasound image volume acquired by the 3D ultrasound transducer.

It will be appreciated by a person skilled in the art that, in general, a larger number of labelled difference images in the training dataset may result in a more accurate deep neural network in classifying future difference image thereto since there is a larger pool of training sample to train the deep neural network. Therefore, it will be appreciated by a person skilled in the art that the non-limiting embodiments are not limited to any specific number of labelled difference images in the training dataset, and any number of labelled difference images may be included in the training dataset as desired or as appropriate.

It will also be appreciated by a person skilled in the art that a deep neural network can be trained based on a training dataset in accordance with various conventional deep learning techniques known in the art, and thus, it is not necessary to describe herein in detail on specifically how a deep neural network is trained based on a training dataset, of which is known in the art. Accordingly, it will be appreciated by a person skilled in the art that the non-limiting embodiments are not limited to any specific type of deep neural network, as long as the deep neural network is capable of being trained to classify a difference image into one of a plurality of classes, the plurality of classes corresponding to a plurality of distance values, respectively. By way of example only and without limitation, various types of deep neural network include a convolutional neural network (CNN), a fully connected network (FCN), a Capsule network and so on. Another method may be to extract features from the difference image and use other types of classifiers, such as but not limited to, SVM, Random Forests and so on.

In various embodiments, the difference image comprises pixels, each pixel having a difference pixel value determined based on a difference between pixel values of corresponding pixels of the pair of consecutive 2D ultrasound images, that is, between a pixel value of a corresponding pixel of one of the pair of consecutive 2D ultrasound images and a pixel value of a corresponding pixel of the other one of the pair of consecutive 2D ultrasound images. For example, a difference image of two images may be generated by subtracting one image from the other image of the two images.

In various embodiments, the step 106 of modifying the number of 2D ultrasound images comprises removing each 2D ultrasound image of the series of 2D ultrasound images that satisfies a predetermined image removal condition; and inserting one or more additional 2D ultrasound images in between each pair of consecutive 2D ultrasound images that satisfies a predetermined image insertion condition.

In various embodiments, the one or more additional 2D ultrasound images are each generated based on an interpolation of the pair of consecutive 2D ultrasound images in between which the one or more additional 2D ultrasound images are to be inserted.

In various embodiments, the plurality of distance values of the plurality of classes, respectively, do not overlap (are each different from one another) and are each configured based on a scan resolution (e.g., a scan resolution of the 3D ultrasound transducer used to acquire one or more 3D ultrasound volumes based on which labelled difference images in a training dataset are obtained). In various embodiments, each of the plurality of distance values may be configured as a multiple of the scan resolution. In various embodiments, the number of classes may be determined based on a distance range desired to be covered by the deep neural network and the scan resolution. By way of an example only and without limitation, if the distance range desired to be covered is 0 to 1 cm and the scan resolution is 0.2 mm, 5 classes may be configured, namely, a first class corresponding to 1× the scan resolution (e.g., 0.2 mm), a second class associated with 2× the scan resolution (e.g., 0.4 mm), a third class associated with 3× the scan resolution (e.g., 0.6 mm) and so on at an interval of 0.2 mm up to a 5th class associated with 5× the scan resolution. In various embodiments, if it is desired to reduce the number of classes (e.g., to reduce complexity), the interval may be increased such as to be at a larger multiple of the scan resolution, e.g., 0.4 mm, 0.6 mm, and so on.

In various embodiments, the scan resolution of the ultrasound transducer may be indicated by the manufacturer or may be determined by examining or experimenting the ultrasound transducer using a pre-calibrated ultrasound phantom.

In various embodiments, the predetermined image removal condition for removing a 2D ultrasound image (e.g., $i^{th}$ image) is based on whether the estimated distance associated with a first pair of consecutive 2D ultrasound images (e.g., $(i-1)^{th}$ image and the $i^{th}$ image) including the 2D ultrasound image (e.g., the $i^{th}$ image) is equal to a predefined multiple of the scan resolution. In various embodiments, the predefined multiple of the scan resolution is one.

In various embodiments, the predetermined image removal condition is further based on whether the estimated distance associated with a second pair of consecutive 2D ultrasound images (e.g., the $i^{th}$ image and $(i+1)^{th}$ image) including the 2D ultrasound image (e.g., the $i^{th}$ image) is equal to the predefined multiple of the scan resolution. In this regard, if the estimated distances associated with the first pair and the second pair are both equal to the predefined multiple of the scan resolution, a distance (which may be referred to as a second distance) between the positions associated with the other 2D ultrasound image (e.g., the $(i-1)^{th}$ image) of the first pair and the other 2D ultrasound image (e.g., the $(i+1)^{th}$ image) of the second pair is estimated based on a classification of a difference image (which may be referred to as a second difference image) generated from the other 2D ultrasound image (e.g., the $(i-1)^{th}$ image) of the first pair and the other 2D ultrasound image (e.g., the $(i-1)^{th}$ image) of the second pair using the deep neural network. In this regard, the predetermined image removal condition is further based on whether the second estimated distance is equal to the predefined multiple of the scan resolution. For example, if both the first pair and the successive second pair are each determined to have an estimated distance of 1× the scan resolution, the distance between the $(i-1)^{th}$ image and the $(i+1)^{th}$ image is further estimated such that if such a distance is estimated to be 1× the scan resolution, the common 2D ultrasound image (e.g., the $i^{th}$ image) amongst the first and second pair may be removed, for example, as being redundant or unnecessary. It will be appreciated by a person skilled in the art that as the deep neural network is trained to classify the difference image to the closest class, for example, a difference image associated with a distance value in between 0 and 1.5× the scan resolution may be classified into the first class corresponding to 1× the scan resolution, a difference image associated with a distance value in between 1.5 and 2.5× the scan resolution may be classified into the second class corresponding to 2× the scan resolution, and so on.

In various embodiments, the predetermined image insertion condition for inserting one or more additional 2D ultrasound images in between a pair of consecutive 2D ultrasound images is based on whether the estimated distance associated with the pair of consecutive 2D ultrasound images is greater than the predefined multiple of the scan resolution. In various embodiments, the number of additional 2D ultrasound images generated is based on the number of times the estimated distance is a multiple of the scan resolution. By way of an example and without limitation, if the estimated distance associated with a pair of consecutive 2D ultrasound images is determined to be 'm' times greater than the scan resolution, the number of additional 2D ultrasound images inserted in between the pair may be 'm−1', and more specifically, one additional 2D ultrasound image at each multiple (i.e., 1 to 'm−1') of the scan resolution such that the large separation between the pair of consecutive 2D ultrasound images may be evenly inserted with additional 2D ultrasound images.

In various embodiments, the predefined multiple of the scan resolution is one. In various other embodiments, the predefined multiple may be other integer as appropriate, such as an integer from 2 to 10.

FIG. 2 depicts a schematic block diagram of a system 200 for generating a 3D ultrasound image of a tissue volume according to various embodiments, such as corresponding to the method 100 for generating a 3D ultrasound image of a tissue volume using at least one processor as described hereinbefore according to various embodiments.

The system 200 comprises an ultrasound transducer 202, a memory 204, and at least one processor 206 communicatively coupled to the memory 204 and the ultrasound transducer 202, and configured to: generate a series of 2D ultrasound images of the tissue volume associated with a plurality of positions, respectively, along a scanning direction of the tissue volume based on a series of ultrasound waves acquired by the ultrasound transducer at the plurality of positions; estimate, for each pair of consecutive 2D ultrasound images of the plurality of 2D ultrasound images, a distance between the positions associated with the pair of consecutive 2D ultrasound images based on a classification of a difference image generated from the pair of consecutive 2D ultrasound images using a deep neural network to produce a plurality of estimated distances associated with the plurality of pairs of consecutive 2D ultrasound images, respectively; modify the number of 2D ultrasound images in the series of 2D ultrasound images based on the plurality of estimated distances to produce a modified set of 2D ultrasound images; and render the 3D ultrasound image of the tissue volume based on the modified series of 2D ultrasound images.

It will be appreciated by a person skilled in the art that the at least one processor 206 may be configured to perform the required functions or operations through set(s) of instructions (e.g., software modules) executable by the at least one processor 206 to perform the required functions or operations. Accordingly, as shown in FIG. 2, the system 200 may further comprise a 2D ultrasound image generator 208 configured to generate a series of 2D ultrasound images of the tissue volume associated with a plurality of positions, respectively, along a scanning direction of the tissue volume based on a series of ultrasound waves acquired by the ultrasound transducer at the plurality of positions; a distance estimator (or distance predictor) 210 configured to estimate, for each pair of consecutive 2D ultrasound images of the plurality of 2D ultrasound images, a distance between the positions associated with the pair of consecutive 2D ultrasound images based on a classification of a difference image generated from the pair of consecutive 2D ultrasound images using a deep neural network to produce a plurality of estimated distances associated with the plurality of pairs of consecutive 2D ultrasound images, respectively; an image series modifier 212 configured to modify the number of 2D ultrasound images in the series of 2D ultrasound images based on the plurality of estimated distances to produce a modified series of 2D ultrasound images; and a 3D image generator 214 configured to render the 3D ultrasound image of the internal anatomical structure based on the modified series of 2D ultrasound images.

It will be appreciated by a person skilled in the art that the above-mentioned modules are not necessarily separate modules, and one or more modules may be realized by or implemented as one functional module (e.g., a circuit or a software program) as desired or as appropriate without deviating from the scope of the present claims. For example, the 2D ultrasound image generator 208, the distance estimator 210, the image series modifier 212, and/or the 3D image generator 214 may be realized (e.g., compiled together) as one executable software program (e.g., software application or simply referred to as an "app"), which for example may be stored in the memory 204 and executable by the at least one processor 206 to perform the functions/operations as described herein according to various embodiments.

In various embodiments, the system 200 corresponds to the method 100 as described hereinbefore with reference to FIG. 1, therefore, various functions or operations configured to be performed by the least one processor 206 may correspond to various steps of the method 100 described hereinbefore according to various embodiments, and thus need not be repeated with respect to the system 200 for clarity and conciseness. In other words, various embodiments described herein in context of the methods are analogously valid for the respective systems or devices, and vice versa.

For example, in various embodiments, the memory 204 may have stored therein the 2D ultrasound image generator 208, the distance estimator 210, the image series modifier 212 and/or the 3D image generator 214, which respectively correspond to various steps of the method 100 as described hereinbefore, which are executable by the at least one processor 206 to perform the corresponding functions/operations as described herein.

A computing system, a controller, a microcontroller or any other system providing a processing capability may be provided according to various embodiments in the present disclosure. Such a system may be taken to include one or more processors and one or more computer-readable storage mediums. For example, the system 200 described hereinbefore may include a processor (or controller) 206 and a computer-readable storage medium (or memory) 204 which are for example used in various processing carried out therein as described herein. A memory or computer-readable storage medium used in various embodiments may be a volatile memory, for example a DRAM (Dynamic Random Access Memory) or a non-volatile memory, for example a PROM (Programmable Read Only Memory), an EPROM (Erasable PROM), EEPROM (Electrically Erasable PROM), or a flash memory, e.g., a floating gate memory, a charge trapping memory, an MRAM (Magnetoresistive Random Access Memory) or a PCRAM (Phase Change Random Access Memory).

In various embodiments, a "circuit" may be understood as any kind of a logic implementing entity, which may be special purpose circuitry or a processor executing software stored in a memory, firmware, or any combination thereof. Thus, in an embodiment, a "circuit" may be a hard-wired logic circuit or a programmable logic circuit such as a programmable processor, e.g., a microprocessor (e.g., a Complex Instruction Set Computer (CISC) processor or a Reduced Instruction Set Computer (RISC) processor). A "circuit" may also be a processor executing software, e.g., any kind of computer program, e.g., a computer program using a virtual machine code, e.g., Java. Any other kind of implementation of the respective functions which will be described in more detail below may also be understood as a "circuit" in accordance with various alternative embodiments. Similarly, a "module" may be a portion of a system according to various embodiments and may encompass a "circuit" as above, or may be understood to be any kind of a logic-implementing entity therefrom.

Some portions of the present disclosure are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as "generating", "estimating", "modifying", "rendering" or the like, refer to the actions and processes of a computer system, or similar electronic device, that manipulates and transforms data represented as physical quantities within the computer system into other data similarly represented as physical quantities within the computer system or other information storage, transmission or display devices.

The present specification also discloses a system, a device or an apparatus for performing the operations/functions of the methods described herein. Such a system, device or apparatus may be specially constructed for the required purposes, or may comprise a general purpose computer or other device selectively activated or reconfigured by a computer program stored in the computer. The algorithms presented herein are not inherently related to any particular computer or other apparatus. Various general-purpose machines may be used with computer programs in accordance with the teachings herein. Alternatively, the construction of more specialized apparatus to perform the required method steps may be appropriate.

In addition, the present specification also at least implicitly discloses a computer program or software/functional module, in that it would be apparent to the person skilled in the art that the individual steps of the methods described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the scope of the claims. It will be appreciated by a person skilled in the art that various modules described herein (e.g., the 2D ultrasound image generator 208, the distance estimator 210, the image series modifier 212, and/or the 3D image generator 214) may be software module(s) realized by computer program(s) or set(s) of instructions executable by a computer processor to perform the required functions, or may be hardware module(s) being functional hardware unit(s) designed to perform the required functions. It will also be appreciated that a combination of hardware and software modules may be implemented.

Furthermore, one or more of the steps of a computer program/module or method described herein may be performed in parallel rather than sequentially. Such a computer program may be stored on any computer readable medium. The computer readable medium may include storage devices such as magnetic or optical disks, memory chips, or other storage devices suitable for interfacing with a general purpose computer. The computer program when loaded and executed on such a general-purpose computer effectively results in an apparatus that implements the steps of the methods described herein.

In various embodiments, there is provided a computer program product, embodied in one or more computer-readable storage mediums (non-transitory computer-readable storage medium), comprising instructions (e.g., the 2D ultrasound image generator 208, the distance estimator 210, the image set modifier 212, and/or the 3D image generator 214) executable by one or more computer processors to perform a method 100 for generating a 3D ultrasound image of a tissue volume as described hereinbefore with reference to FIG. 1. Accordingly, various computer programs or modules described herein may be stored in a computer program product receivable by a system (e.g., a computer system or an electronic device) therein, such as the system 200 as shown in FIG. 2, for execution by at least one processor 206 of the system 200 to perform the required or desired functions.

The software or functional modules described herein may also be implemented as hardware modules. More particularly, in the hardware sense, a module is a functional hardware unit designed for use with other components or modules. For example, a module may be implemented using discrete electronic components, or it can form a portion of an entire electronic circuit such as an Application Specific Integrated Circuit (ASIC). Numerous other possibilities exist. Those skilled in the art will appreciate that the software or functional module(s) described herein can also be implemented as a combination of hardware and software modules.

It will be appreciated by a person skilled in the art that the system 200 may made up of separate units or as one integrated unit. For example, in various embodiments, the system 200 may comprise a computer system including the one or more processor 206, the memory 204, the 2D ultrasound image generator 208, the distance estimator 210, the image set modifier 212, and the 3D image generator 214, and a separate ultrasound probe including the ultrasound transducer 202 communicatively coupled to the computer system. In other words, the separate ultrasound probe may acquire a series of ultrasound waves with respect to a tissue volume, and the series of ultrasound waves may then be transmitted (e.g., based on wireless or wired communication) to the computer system at a different location for performing the method of generating a 3D ultrasound image of the tissue volume as described hereinbefore with reference to FIG. 1. In various other embodiments, the system 200 may correspond to, or may be embodied as, an ultrasound probe, including the ultrasound transducer 202, the one or more processor 206, the memory 204, the 2D ultrasound image generator 208, the distance estimator 210, the image set modifier 212, and the 3D image generator 214.

Figure 3:
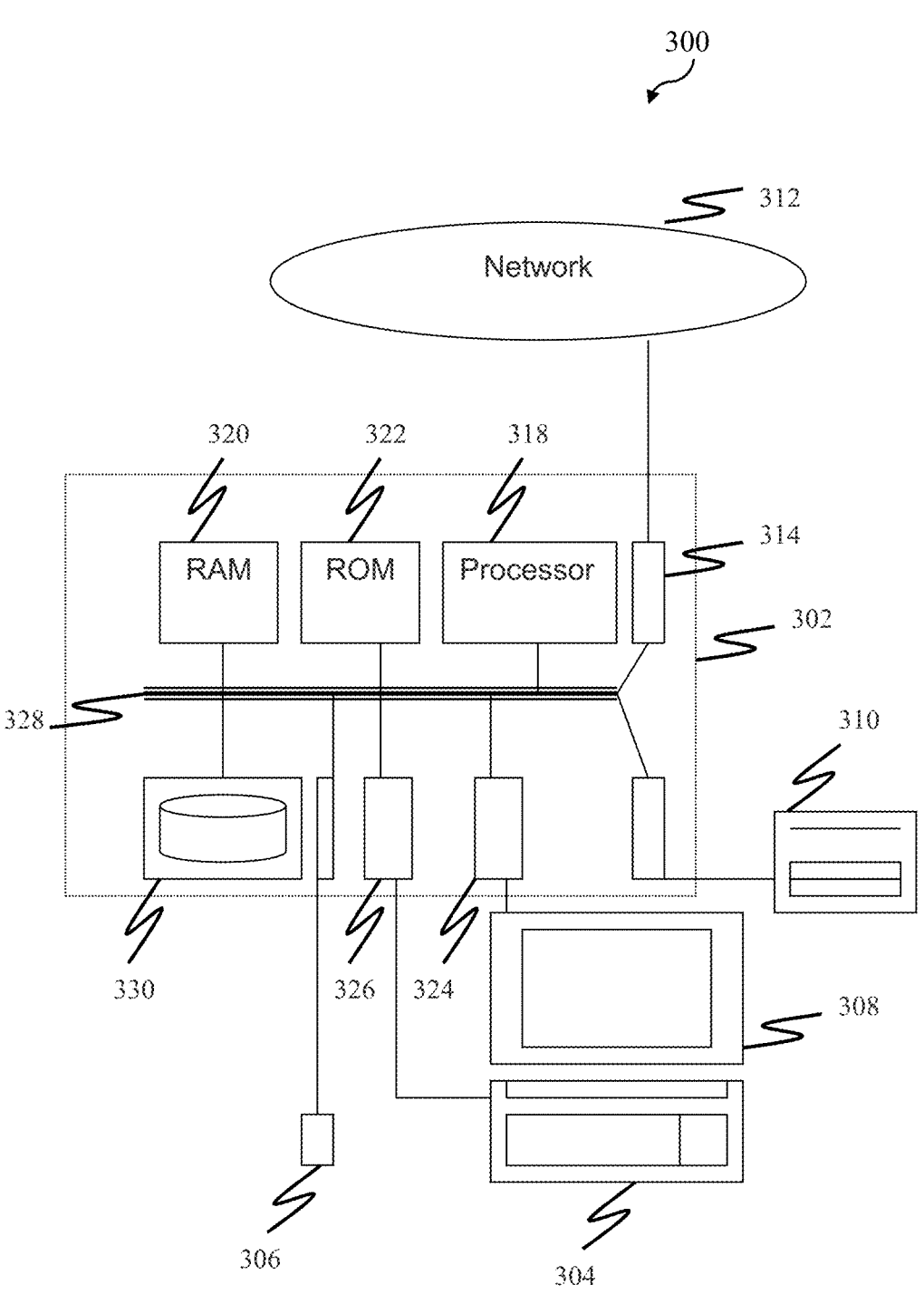
FIG. 3 depicts a schematic block diagram of an exemplary computer system which may be used to realize or implement the system for generating a 3D ultrasound image of a tissue volume according to various embodiments, such as the system as depicted in FIG. 2.

In various embodiments, the above-mentioned computer system may be realized by any computer system (e.g., portable or desktop computer system), such as a computer system 300 as schematically shown in FIG. 3 as an example only and without limitation. Various methods/steps or functional modules (e.g., the 2D ultrasound image generator 208, the distance estimator 210, the image set modifier 212, and/or the 3D image generator 214) may be implemented as software, such as a computer program being executed within the computer system 300, and instructing the computer system 300 (in particular, one or more processors therein) to conduct the methods/functions of various embodiments described herein. The computer system 300 may comprise a computer module 302, input modules, such as a keyboard 304 and a mouse 306, and a plurality of output devices such as a display 308, and a printer 310. The computer module 302 may be connected to a computer network 312 via a suitable transceiver device 314, to enable access to e.g. the Internet or other network systems such as Local Area Network (LAN) or Wide Area Network (WAN). The computer module 302 in the example may include a processor 318 for executing various instructions, a Random Access Memory (RAM) 320 and a Read Only Memory (ROM) 322. The computer module 302 may also include a number of Input/Output (I/O) interfaces, for example I/O interface 324 to the display 308, and I/O interface 326 to the keyboard 304. The components of the computer module 302 typically communicate via an interconnected bus 328 and in a manner known to the person skilled in the relevant art.

It will be appreciated by a person skilled in the art that the terminology used herein is for the purpose of describing various embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Various example embodiments will be described hereinafter by way of examples only and not limitations. It will be appreciated by a person skilled in the art that the present invention may, however, be embodied in various different forms or configurations and should not be construed as limited to the example embodiments set forth hereinafter. Rather, these example embodiments are provided so that this disclosure will be thorough and complete, and will fully convey the scope of the present invention to those skilled in the art.

Various example embodiments relate to ultrasound imaging, and more particularly, to the reconstruction of a complete 3D ultrasound volume from freehand 2D ultrasound sweep scans. The 3D ultrasound images may be constructed (rendered) by precisely estimating the distance between each pair of consecutive 2D ultrasound images (which may also be referred to as 2D slices or frames) obtained using a deep learning neural network specifically trained for distance prediction. In this regard, it is noted that estimation of the inter-scan distance is non-trivial for freehand scanning without position tracking as there is no external point of reference for the ultrasound image, unlike for example, Magnetic Resonance Imaging (MRI).

In various example embodiments, there is provided a method for generating a 3D ultrasound image of a tissue volume without utilizing position tracking (which may also be referred as being sensorless) and speckle decorrelation. In contrast, various example embodiments directly estimate the physical distance between a pair of consecutive 2D ultrasound images using a convolutional neural network (CNN) and reconstructs a complete 3D ultrasound volume (3D ultrasound image) from the 2D ultrasound images acquired from the freehand 2D ultrasound sweep scans. Such an approach significantly reduces costs as it is possible to generate a 3D ultrasound volume using a low cost 2D ultrasound probe instead of a relatively expensive 3D ultrasound probe. It has also been found that the 3D ultrasound volumes generated according to the method according to various example embodiments are satisfactorily similar in quality to 3D ultrasound volumes from a 3D ultrasound probe (i.e., direct 3D ultrasound scanning using a 3D ultrasound probe).

Figure 4:
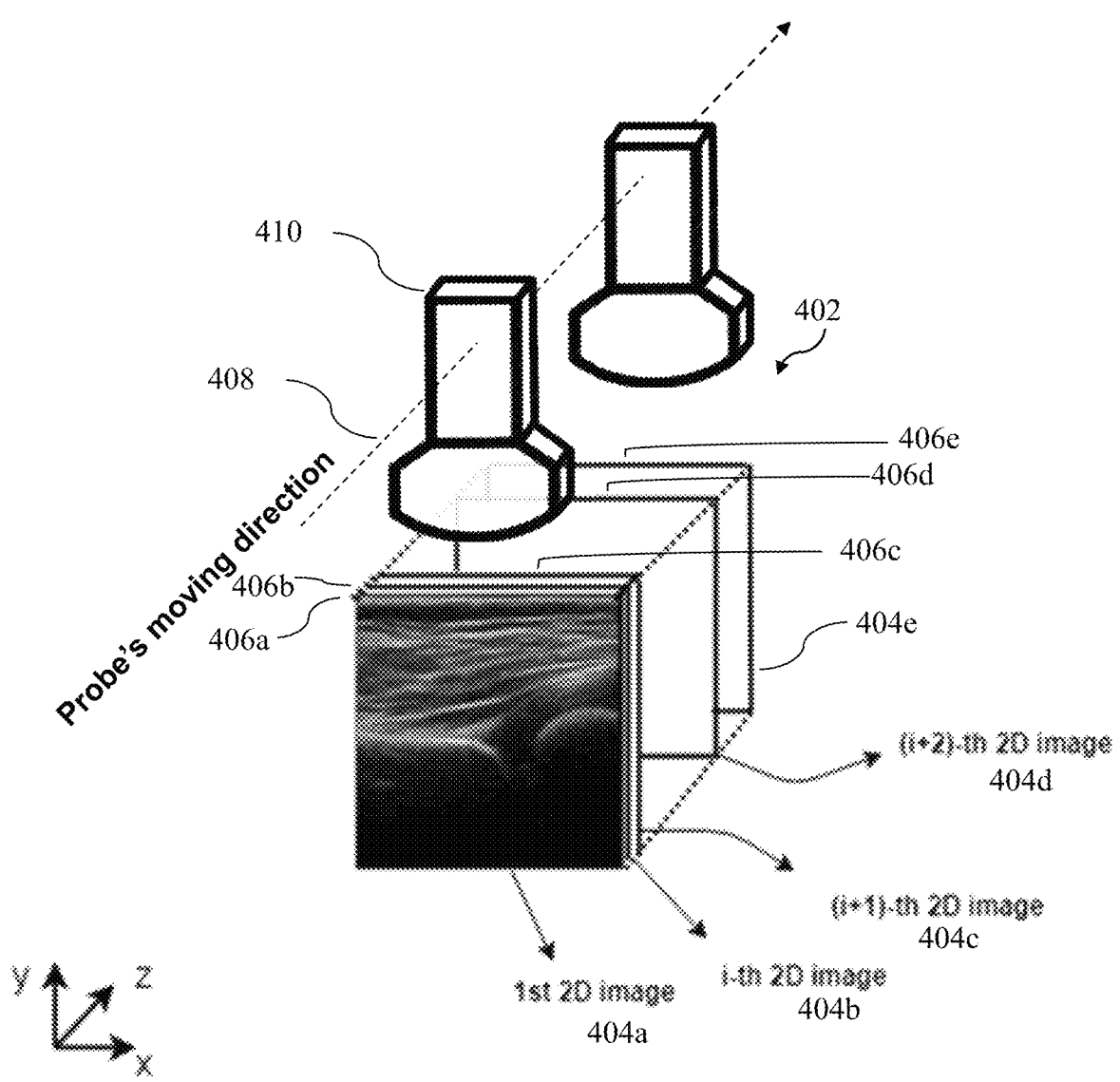
FIG. 4 depicts an example series of 2D ultrasound images of a tissue volume associated with a plurality of positions, respectively, along a scanning direction of the tissue volume which are generated according to various example embodiments.

For illustration purpose only and without limitation, FIG. 4 depicts an example series (or sequence or plurality) 402 of 2D ultrasound images (e.g., 404a, 404b, 404c, 404d, 404e) of a tissue volume associated with a plurality of positions (e.g., 406a, 406b, 406c, 406d, 406e), respectively, along a scanning direction 408 of the tissue volume which are generated according to various example embodiments. In this regard, the series 402 of 2D ultrasound images are generated based on a series of ultrasound waves acquired by the ultrasound transducer (e.g., installed in the ultrasound probe 410) at the plurality of positions (e.g., 406a, 406b, 406c, 406d, 406e) along the ultrasound probe's scanning direction 408.

Figure 5:
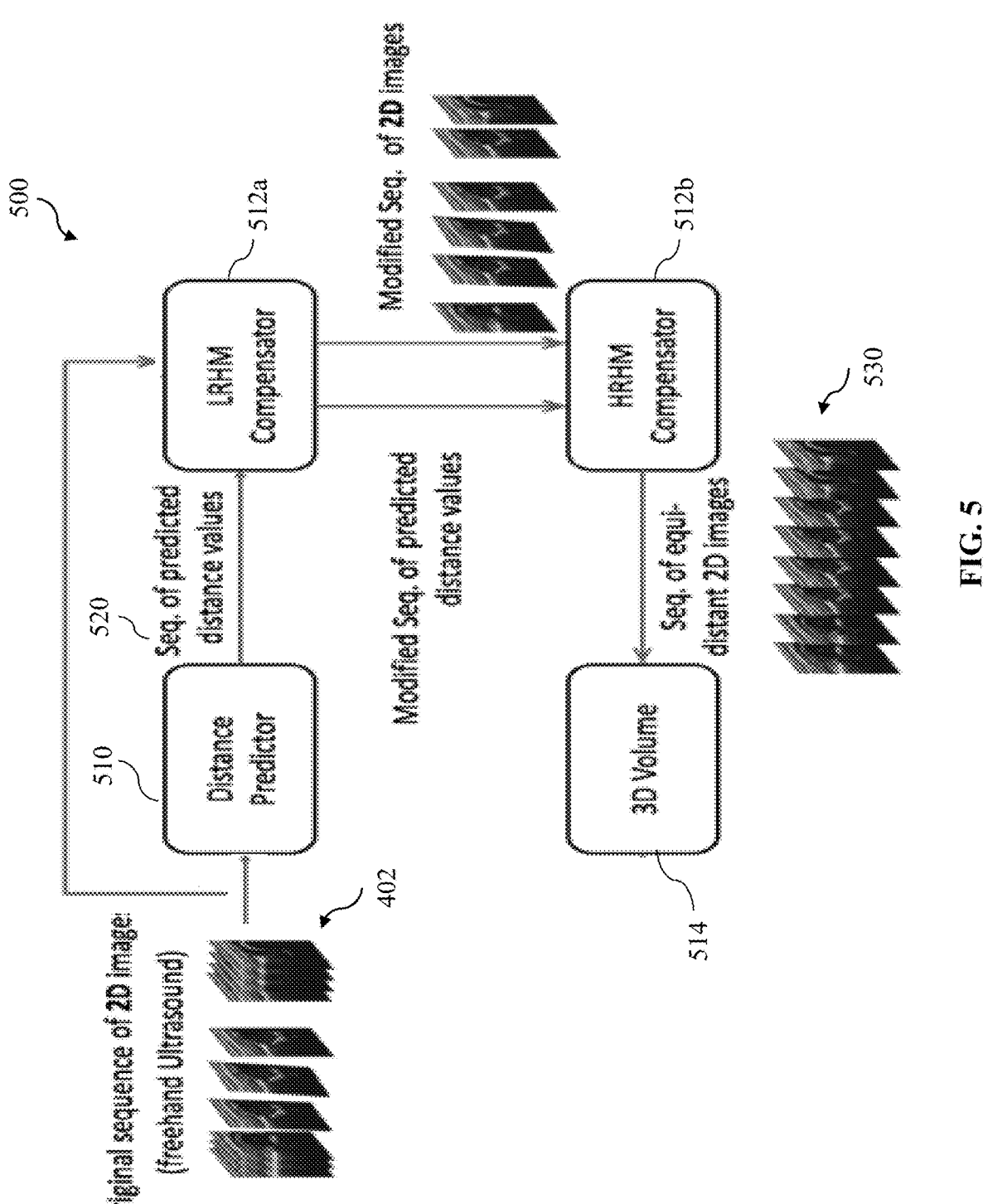
FIG. 5 depicts an overview of an example method for generating a 3D ultrasound image according to various example embodiments.

FIG. 5 depicts an overview of an example method 500 for generating a 3D ultrasound image according to various example embodiments. As shown in FIG. 5, the example method 500 may include four stages (or modules), namely, a distance prediction stage (or a distance predictor) 510, a low rate hand movement (LRHM) compensation stage (or a LRHM compensator) 512a, a high rate hand movement (HRHM) compensation stage (or a HRHM compensator) 512b, and a 3D volume rendering stage (or a 3D volume generator) 514. In various example embodiments, the distance predictor 510 may correspond to the distance estimator 210, the LRHM compensator 512a and the HRHM compensator 512b may correspond to the image series modifier 212 and the 3D volume generator 514 may correspond to the 3D image generator 214 as described hereinbefore according to various embodiments.

The distance predictor 510 may include a CNN trained to predict (estimate) the Euclidean distance in a depth dimension (e.g., the Z-axis shown in FIG. 4, which is an axis parallel to the scanning direction 408, or along an axis perpendicular to the 2D ultrasound image) between consecutive 2D ultrasound scans. The series 402 of 2D ultrasound images may then be modified based on the series (or sequence or plurality) 520 of predicted distances from the distance predictor 510 by the LRHM compensator 512a and the HRHM compensator 512b to, for example, account for variance or inconsistency in the speed of hand movement during the ultrasound scan.

The distance predictor 510 will now be described in further details according to various example embodiments. The distance predictor 510 is configured to directly estimate the distance between adjacent scans in the Z-direction based on a training dataset. For example, advantages associated with the distance predictor 510 include that it does not require additional inputs (e.g., optical flow maps along with the original image) for estimating the distance and that it does not make any assumptions on the structures present in the image data input (difference image). In various example embodiments, a difference image (e.g., pixel-wise intensity difference image) is directly computed for each pair of consecutive 2D ultrasound images of the series 402 of 2D ultrasound images, and such a difference image computed is then used as an input to the distance predictor (e.g., including a CNN) 510. Without wishing to be bound by theory, it is found according to various embodiments that the structure of a tissue volume (e.g., internal anatomical structure) captured in a pair of images with a relatively large separation may likely have a greater change compared to a pair of images with a smaller separation. Therefore, the difference in the pixel intensities, on average, between a pair of images having a relatively large separation may be larger.

Figure 6:
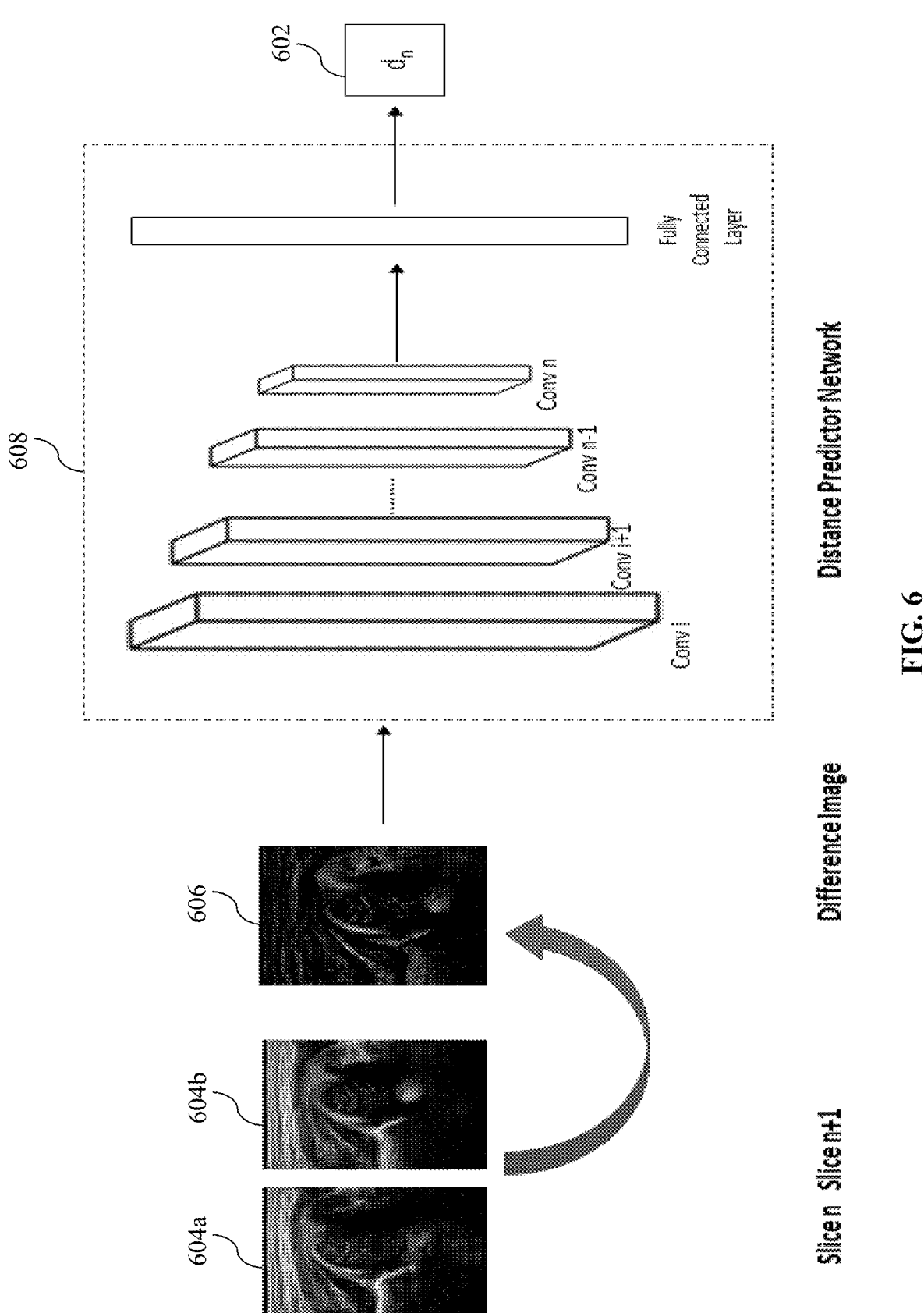
FIG. 6 depicts an overview of steps/operations performed by a distance predictor for estimating a distance between the positions associated with a pair of consecutive 2D ultrasound images according to various example embodiments.

For illustration purpose only and without limitation, FIG. 6 depicts an overview of steps/operations performed by the distance predictor 510 for estimating a distance $(d_n)$ 602 between the positions associated with a pair of consecutive 2D ultrasound images (604a, 604b) according to various example embodiments. As shown in FIG. 6, a difference image 606 is generated from the pair of consecutive 2D ultrasound images (604a, 604b), such as a pixel-wise intensity difference image. Subsequently, the difference image 606 generated is input to the trained distance predictor network (e.g., trained CNN) 608, which then estimates and outputs the distance $(d_n)$ 602 based on the difference image 606 received.

In various example embodiments, the distance predictor network 608 is trained based on a training dataset (e.g., a training sample) comprising a plurality of labelled difference images, each labelled difference image being labelled (or tagged) with a predetermined one of a plurality of classes which the difference image belongs to. For example, each labelled difference image may be obtained by generating a difference image from a pair of 2D ultrasound images obtained at a known distance apart, and then labelling the difference image generated with such a known distance to obtain the labelled difference image. In various example embodiments, the pair of 2D ultrasound images may be two image slices/frames obtained at a desired distance apart from a 3D ultrasound image obtained from direct 3D ultrasound scanning using a 3D ultrasound probe. For example, from the 3D ultrasound image, a set of image slices/frames (2D ultrasound images) may be obtained at a regular or predefined interval apart. In various example embodiments, the predefined interval apart may be configured based on the scan resolution of the 3D ultrasound probe, such as being configured as a multiple of the scan resolution. In a non-limiting example embodiment, the predefined interval is equal to the scan resolution. For example and without limitation, values for the scan resolution may range from 0.1 to 0.3 mm. However, it will be appreciated that the non-limiting embodiments are not limited to such a range of scan resolution as, for example, the scan resolution may increase with improvement in technology. With the set of image slices/frames obtained at a regular interval apart, various pairs of 2D ultrasound images at various distances apart (which will be a multiple of the scan resolution) may be selected based on which corresponding labelled difference images may then be generated for inclusion in the training dataset for training the distance predictor network 608. It will be appreciated by a person skilled in the art that a number of 3D ultrasound images may be obtained and labelled difference images may be derived from each 3D ultrasound image in the same manner as described above for inclusion in the training dataset.

By way of an example only and without limitation, the distance predictor network may be trained to estimate distance into one of six non-overlapping classes as shown in Table 1 below.

TABLE 1

| Classes associated with a Distance Predictor Network (e.g., CNN) and Corresponding Distance Values | |
| --- | --- |
| Class Index | Distance Values in terms of Scan Resolution (r) |
| 1 | 1 × r |
| 2 | 2 × r |
| 3 | 3 × r |
| 4 | 4 × r |
| 5 | 5 × r |
| 6 | 6 × r or above |

In contrast, conventional techniques of determining the distance between a pair of consecutive images may utilize physical measured distances as ground truth, which require additional position sensor(s) or measurement arm(s). In such conventional techniques, the accuracy of the ground truth distances depend on the accuracy of the position sensors. In comparison to such conventional techniques, for example, the method of obtaining the distance between a pair of consecutive images according to various example embodiments is simpler (e.g., does not require tracking hardware) and more reliable (e.g., as its accuracy may be determined by the scan resolution of the 3D ultrasound probe, which may have a scan resolution of about 0.1 mm).

Figure 7:
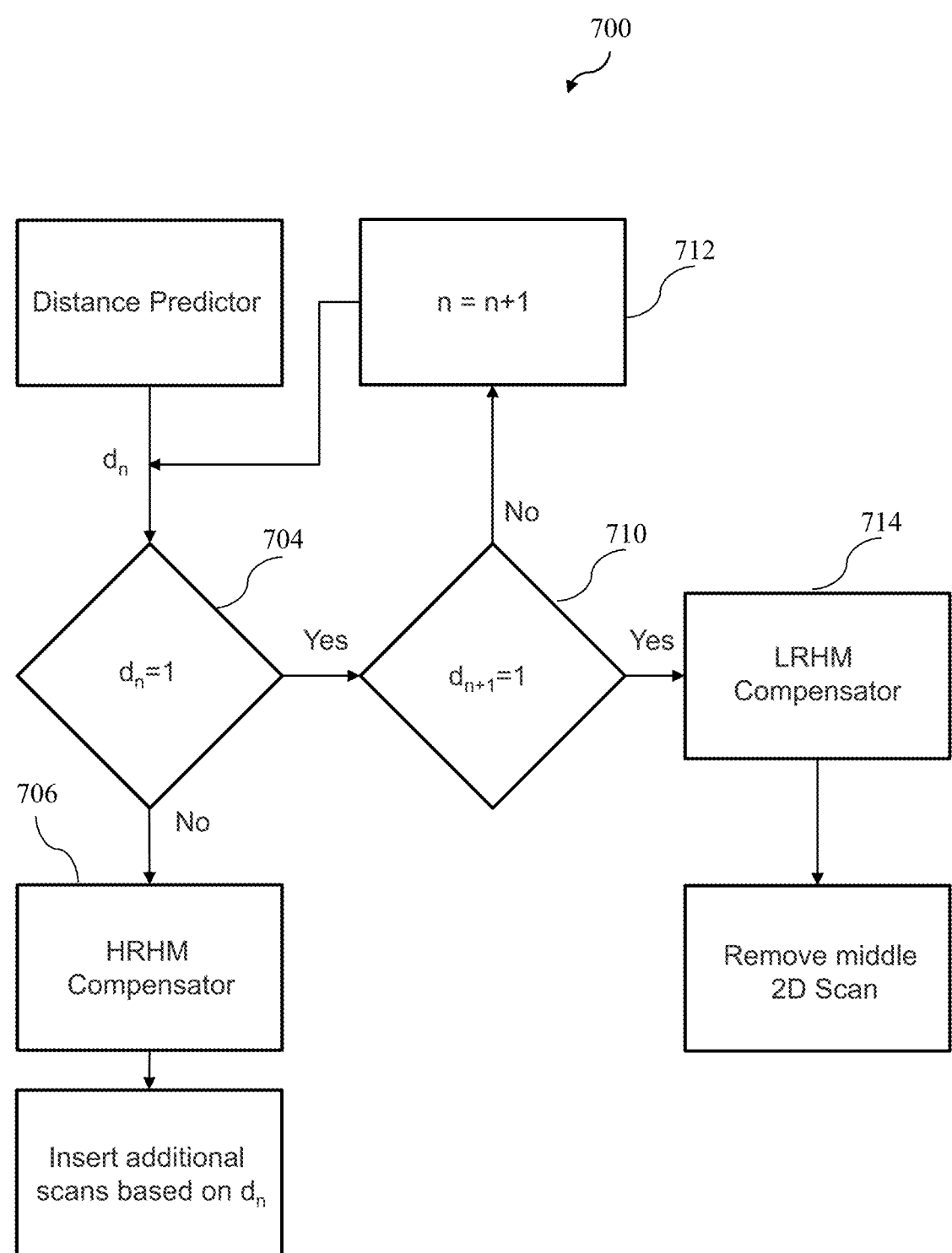
FIG. 7 depicts a flow diagram of a method of modifying the number of 2D ultrasound images in a series of 2D ultrasound images based on a series of estimated distances to produce a modified series of 2D ultrasound images according to various example embodiments.

The LRHM compensator 512a and the HRHM compensator 512b will now be described in further details according to various example embodiments. FIG. 7 depicts a flow diagram of a method 700 of modifying the number of 2D ultrasound images in the series 402 of 2D ultrasound images based on the series 520 of estimated distances to produce a modified series 530 of 2D ultrasound images according to various example embodiments. At 704, the sequence/series 520 of predicted/estimated distances obtained from the distance predictor 510 may be analyzed sequentially. For example, it is determined whether a first predicted distance ($d_n$) of the series 520 of predicted distances is equal to 1 (which is the predefined multiple of the scan resolution in the example embodiment of FIG. 7). If the first predicted distance is not equal to 1 (and thus, the predicted distance is an integer greater than 1), at 706, the HRHM compensator 512b may be activated to insert additional 2D ultrasound image(s) in between the corresponding pair of consecutive 2D ultrasound images. In a non-limiting embodiment, the number ('a') of additional 2D ultrasound images inserted is based on the number of times ('m') the estimated distance is a multiple of the scan resolution, such as a=m−1. In a non-limiting embodiment, the one or more additional 2D ultrasound images are each generated based on an interpolation of the corresponding pair of consecutive 2D ultrasound images in between which the one or more additional 2D ultrasound images are to be inserted.

On the other hand, if the first predicted distance is equal to 1, at 710, it is determined whether a second predicted distance ($d_{n+1}$) next in sequence/series is equal to 1. If the second predicted distance is not equal to 1 (and thus, the predicted distance is an integer greater than 1), at 712, the count 'n' (of the n-th predicted distance in the series 520 of predicted distances) is incremented by 1 (i.e., n=n+1) and the method/process 700 returns to 704 to analyze the next predicted distance in the series 520 of predicted distances. On the other hand, if the second predicted distance is equal to 1, at 714, the LRHM compensator 512a may be activated to determine whether to remove the 2D ultrasound image (e.g., $i^{th}$ image) that is common to both the first and second pair of consecutive 2D ultrasound images associated with the first and second predicted distances. In this regard, the LRHM compensator 512a may be configured to request or activate the distance predictor 510 to estimate a distance (e.g., a second distance) between the first 2D ultrasound image (e.g., the $(i−1)^{th}$ image) in sequence in the first pair and the second 2D ultrasound image (the $(i+1)^{th}$ image) in sequence in the second pair. In this regard, if the second distance is estimated to be equal to 1, the above-mentioned common 2D ultrasound image (e.g., $i^{th}$ image) is removed.

Figure 8:
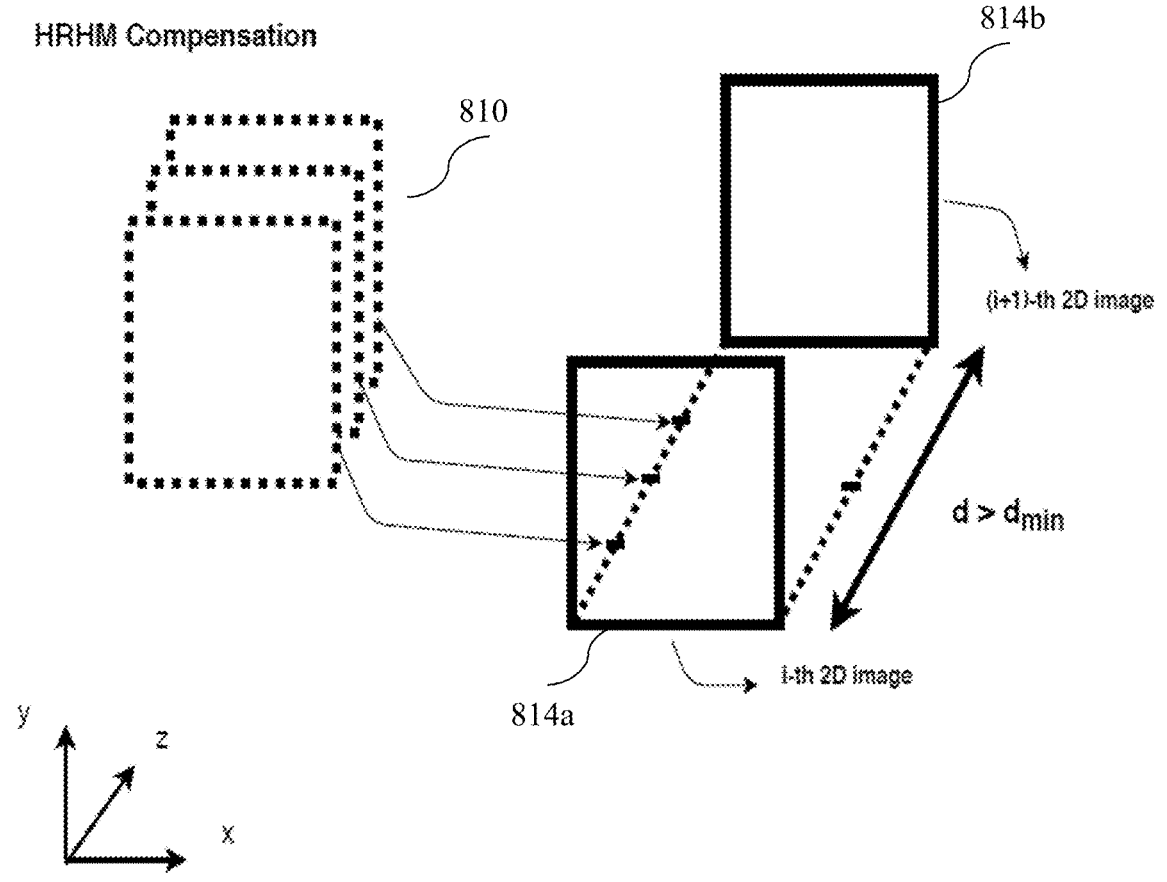
FIG. 8 depicts an example insertion of interpolated 2D ultrasound images in between a pair of 2D ultrasound images according to various example embodiments.

Accordingly, the HRHM compensator 512b advantageously accounts for a high rate of hand movement during the ultrasound scanning, which would otherwise result in larger than desired distances between adjacent scans (d>1). For example, the HRMH compensator 512b may be configured to linearly interpolate between a pair of 2D ultrasound images based on the predicted distance between the pair. As an example, it is noted that the structural details of a bony structure as a hip at a distance of 0.5 mm apart may not vary much, and hence, the linear interpolation may be most suitable in such a case. However, it will be appreciated by a person skilled in the art that the non-limiting embodiments are not limited to any particular type of interpolation, and other types of interpolation may be applied as desired or as appropriate, such as but not limited to, bicubic spline interpolation, polynomial interpolation or piecewise constant interpolation. By way of an example, assuming that the predicted distance is 4×r, the HRHM compensator 512b may be configured to insert (e.g., evenly) three interpolated 2D ultrasound images (slices) 810 in between the corresponding pair of 2D ultrasound images (814a, 814b) as illustrated in FIG. 8. These interpolated 2D ultrasound images (slices) 810 compensate for the slices that were not captured due to the high rate of scanning. The HRHM compensator 512b thus advantageously facilitates the modified series of 2D ultrasound images to be periodic in space, which in turn results in a smooth 3D ultrasound volume rendered based on the modified series of 2D ultrasound images.

Figure 9:
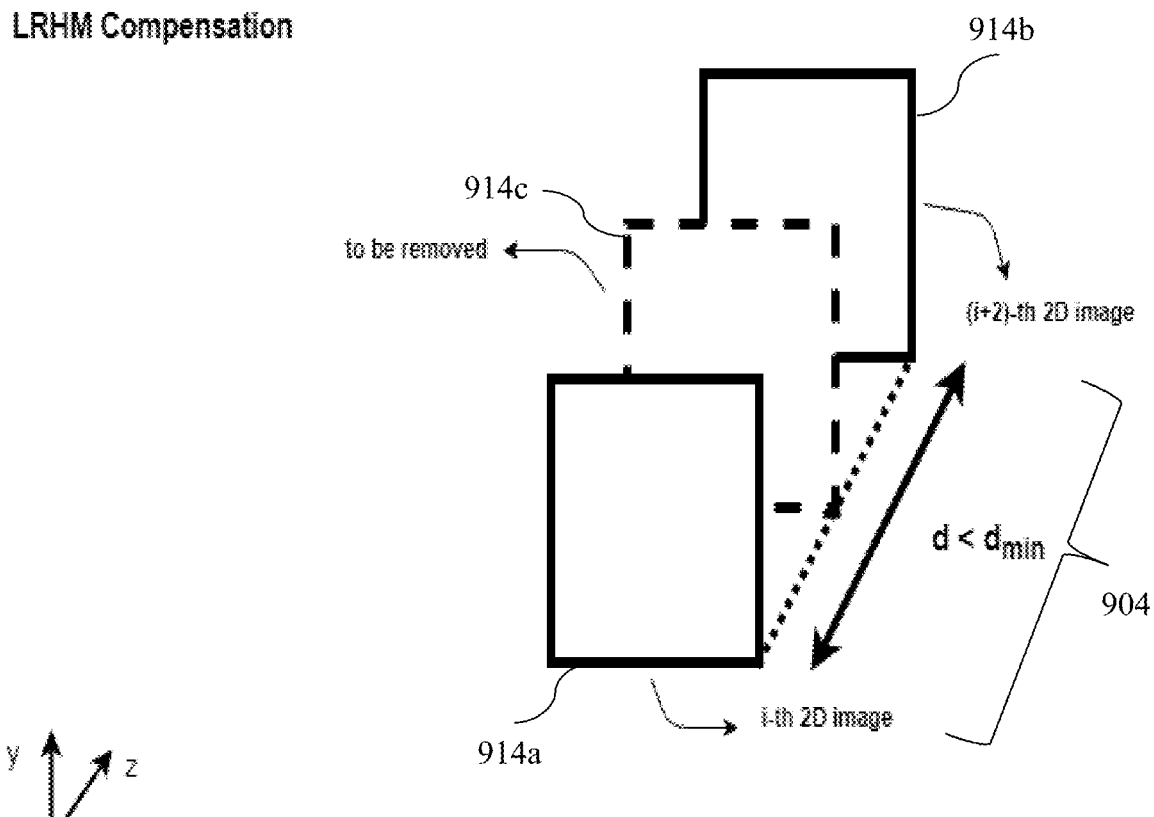
FIG. 9 depicts an example removal of a 2D ultrasound image in between a pair of 2D ultrasound images according to various example embodiments.

The LRHM compensator 512a advantageously accounts for a low rate of hand movement during the ultrasound scanning, which would otherwise result in multiple 2D ultrasound images being acquired at the same physical location or very close to each other (e.g., less than the scan resolution), which do not add any extra or further structural information useful for rendering the 3D ultrasound volume. For each pair of such 2D ultrasound images, as described hereinbefore, the distance predictor 510 may be configured to classify the pair (i.e., its difference image) into a first class corresponding to 1× the scan resolution (r), that is, estimating the distance (d) between the pair as 1×r. For example, the LRHM compensator 512a may be configured to identify each cluster (or group) 904 of two consecutive predicted distance values (i.e., length of 2) in the series 520 of predicted distance values having the value of 1×r. Each of such cluster 904 would consist of 3 slices (2D ultrasound images) and the distance between the first slice (e.g., $i^{th}$ slice) 914a and the third slice (e.g., $(i+2)^{th}$ slice) 914b is estimated using the distance predictor 510. If the estimated distance is 1, then the middle slice 914c in the cluster (e.g., $(i+1)^{th}$ slice) is discarded as shown in FIG. 9. This is because if the distance between the first and third slices is estimated to be 1, then the middle slice has a distance less than the scan resolution from both the first and the third slices. Therefore, the middle slice is considered to not add any extra or further structural information useful for rendering the 3D ultrasound volume and may thus be removed. The above process is repeated over the sequence 520 of predicted distance values for each of such cluster identified.

By way of an example and without limitation, a specific example implementation of the distance predictor 510 including a convolutional neural network (CNN) known as VGG-16 will now be described. However, as explained hereinbefore, it will be appreciated that the non-limiting embodiments are not limited to a CNN, let alone VGG-16. The VGG-16 network includes 16 layers (i.e., 13 convolutional layers and 3 fully connected layers). The algorithms are written in Python 3.5, and the TFLearn framework (e.g., such as described in Tang, Yuan, "TF. Learn: TensorFlow's High-level Module for Distributed Machine Learning", arXiv preprint arXiv:1612.04251(2016), the content of which is hereby incorporated by reference in its entirety for all purposes) was used for training the VGG-16 network (e.g., such as described in Simonyan, Karen, and Andrew Zisserman, "Very Deep Convolutional Networks for Large-scale Image Recognition", arXiv preprint arXiv:1409.1556 (2014), the content of which is hereby incorporated by reference in its entirety for all purposes). Various components of the CNN in the context of VGG-16 will now be described.

Convolutional Layers

Each convolutional layer may have three components, namely, convolution kernels/filters, non-linear activation functions, and pooling.

Convolution Kernels/Filters

The convolution operator generates a linear combination of the input image based on a set of weights (W). Unlike traditional approaches where the mapping is handcrafted, CNNs learn the mapping from the image data in order to solve a target problem, which according to various embodiments is estimating the distance between a pair of 2D ultrasound images. The convolution operator accounts for the neighbourhood of a pixel and is translation invariant. In VGG-16, 3×3 convolution kernels may be provided in each layer. Each convolution analyzes the image data at a particular scale and captures various features as a feature map.

Non-Linear Activation Functions

In order to obtain a non-linear mapping, the linear filter output is used as the input of a non-linear activation function applied identically to each neuron in a feature map. In the example implementation, Rectified Linear Unit (ReLU) was used as the non-linear activation function in this network.

Pooling

The third component of a convolutional layer is pooling. A pooling operator operates on individual feature channels, combining nearby feature values into one by the application of a suitable operator. For example, common choices include max-pooling (using the max operator) or sum-pooling (using summation). In the example implementation, max-pooling was used.

In the example implementation, the number of kernels used in each of the convolutional layers is summarized in Table 2 below.

TABLE 2

| Number of filters used in each convolutional layer in VGG-16 | |
|---|---|
| Layer | Number of Kernels/Filters |
| 1-2 | 64 |
| 3-4 | 128 |
| 5-7 | 256 |
| 8-13 | 512 |

It will be appreciated by a person skilled in the art that the specific configuration shown in Table 2 is only an example implementation and is not limited to the specification configuration shown.

Fully Connected Layers

In a fully-connected layer, each neuron of one layer is connected to all neurons in subsequent layers. In this regard, VGG-16 has 4096 neurons in each fully connected layer and the output of each of the neurons are passed to a RELU activation function.

Example Training Implementation

As a non-limiting example, 725 training examples (i.e., 725 different pairs of 2D ultrasound images) were selected from a 3D ultrasound volume. The size of the validation set is set to 80. The input shape of the network is 224×224×3, where all the channels were filled with the corresponding difference images. Every sample in training dataset was normalized with the mean computed over all the training examples. Adaptive gradient algorithm, i.e., AdaGrad, was used as the optimizer. The activation function "softmax" was used for the last layer with six classes. In addition, the loss function used was "categorical cross-entropy". Batch size, number of epochs and learning rate were set to 64, 50 and 0.001, respectively. The scan resolution of the 3D ultrasound probe was 0.14 mm in the Z direction. The approximate prediction and pre-processing time were 24 and 9 seconds on a GPU, i.e., Tesla K 80, 12 GB GDDR5.

The VGG-16 network was tested on three different 3D ultrasound volumes with accuracies 0.95%, 0.92% and 0.88%, respectively. Table 3 provides a summary of the training information in the example training implementation.

TABLE 3

| Summary of the Example Training Implementation | | | | | |
|---|---|---|---|---|---|
| Network | resolution | Training size | Validation size | Batch size | Number of epochs | Learning rate |
| VGG16 | 0.14 mm | 725 | 80 | 64 | 50 | 0.001 |

It will be appreciated by a person skilled in the art that the non-limiting embodiments are not limited to the specific example implementation of the distance predictor 510 and any type of deep neural network may be implemented, along with suitable parameters/settings, as desired or as appropriate, in relation to the distance predictor. For example, in the case of CNN, the CNN may also be implemented with fully connected layers alone. For example, activation functions may also be extended to Sigmoid function. For example, Adam, SGD or other types of algorithms may be used for the optimizer. For example, the distance predictor 510 may also be implemented using other versions of VGG, such as VGG-19, or other types of pre-trained networks, such as ResNet50, Inception V3, and Xception. A 3D network may also be used for distance prediction.

As an example use case for illustration purpose only and without limitation, a method for generating a 3D ultrasound image according to various example embodiment was performed with respect to an infant hip joint. For example, ultrasound examination of the hip joint in infants is crucial in the diagnosis of hip dysplasia. The distance predictor network was trained using only one 3D ultrasound volume, with 800 training examples derived from the 3D ultrasound volume in total, of the hip scanned using a Philips iU22 scanner (Philips Healthcare, Andover, Mass) using a 13 MHz linear (Philips 13VL5) transducer in coronal orientation and exported to cartesian DICOM. Each 3D ultrasound comprises 256 ultrasound slices of 0.13 mm thickness, each slice containing 411×192 pixels and each pixel measuring 0.11×0.20 mm.

The method was then tested on different 3D volumes where the average accuracy of the predicted distance values was found to be 92%. The method was also tested on 2D ultrasound sweeps acquired at various rates of hand movement scanned using a 2D ultrasound probe. In all cases, it was found that the method was able to generate a smooth 3D ultrasound volume from the sequence of 2D ultrasound scans. The reconstructed 3D ultrasound volumes generated from the method were qualitatively evaluated by an expert radiologist and found to closely correlate with the corresponding 3D ultrasound images.

Figure 10A:
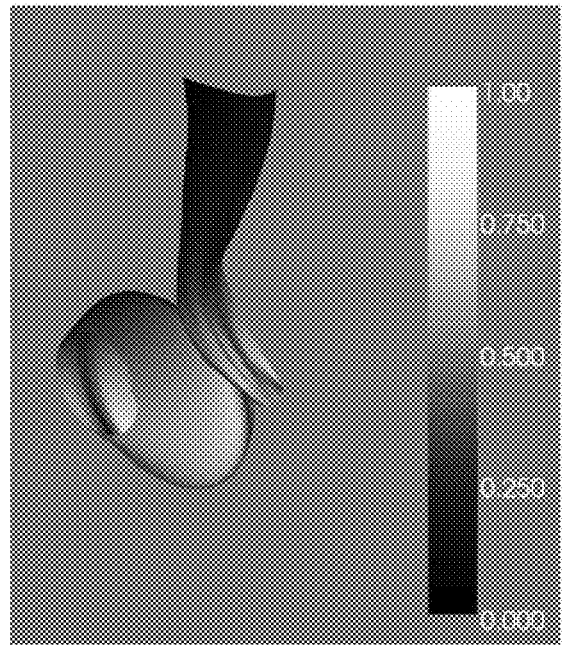
FIGS. 10A and 10B depict an example overlay of 3D segmentation meshes obtained based on a modified 2D sweep and an unmodified 2D sweep according to various example embodiments.
Figure 10B:
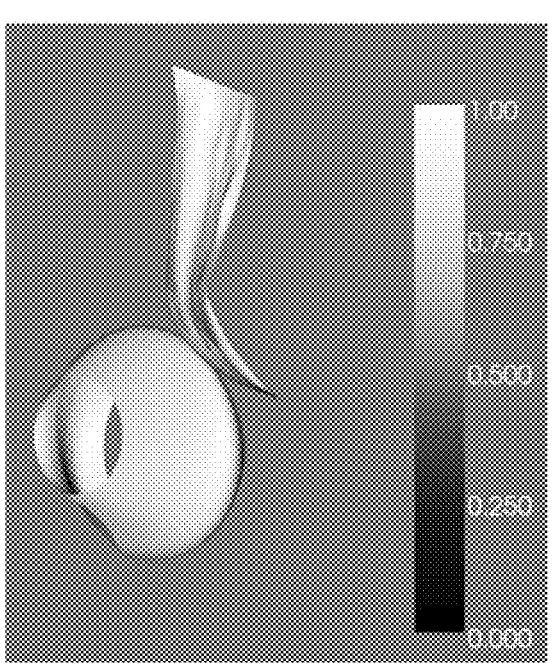

The method was further validated experimentally by comparing segmentations of the hip bone obtained from a 3D scan ultrasound volume (3D scan model) with segmentations obtained from an unmodified 2D sweep (i.e., without the series of 2D ultrasound images being modified as described according to various embodiments) and from a modified 2D sweep (i.e., with the series of 2D ultrasound images being modified as described according to various embodiments) for the same patient. An overlay of the 3D segmentation meshes obtained in each case is shown in FIGS. 10A and 10B. In FIGS. 10A and 10B, the lighter shades indicate a higher distance value (distance difference) with white colour indicating the highest and black colour indicating the lowest. It can be seen in FIG. 10B that considerably large regions in the model segmented from the unmodified 2D sweep have bright regions indicating large difference in distance from the 3D scan model. On the other hand, as can be seen in FIG. 10A, the corresponding regions in the modified 2D sweep have lower values of distance (i.e., lower distance differences) and are hence darker in color. The mean distance difference between the segmentations obtained from the modified 2D sweep and the 3D scan model was 0.4 mm, which indicates that the structural information in the modified 2D sweep acquired from the 2D ultrasound probe closely correlates to the 3D scan model (3D ultrasound volume) obtained directly from the 3D ultrasound probe.

While embodiments have been particularly shown and described with reference to specific embodiments, it should be understood by those skilled in the art that various changes in form and detail may be made therein without departing from the spirit and scope as defined by the appended claims. The scope is thus indicated by the appended claims and all changes which come within the meaning and range of equivalency of the claims are therefore intended to be embraced.

What is claimed is:

1. A method, comprising:
generating a series of two-dimensional (2D) ultrasound images of a tissue volume associated with a plurality of positions, respectively, along a scanning direction of the tissue volume;
for a pair of consecutive 2D ultrasound images of the series of 2D ultrasound images, using a deep neural network to classify a difference between the pair of consecutive 2D ultrasound images of the series of 2D ultrasound images, wherein the deep neural network is trained to classify differences between images based on one of a plurality of predefined classes;
modifying a number of 2D ultrasound images in the series of 2D ultrasound images based on the classification of the difference between the pair of consecutive 2D ultrasound images of the series of 2D ultrasound images, thereby producing a modified series of 2D ultrasound images; and
performing a measurement of tissue using at least one of the modified series of 2D ultrasound images.

2. The method of claim 1, further comprising rendering a 3D ultrasound image of the tissue based on the modified series of 2D ultrasound images.

3. The method of claim 2, wherein the tissue is rendered on a portable computing system.

4. The method of claim 1, wherein the plurality of predefined classes correspond to a plurality of distance values, respectively, and the method further comprises estimating a distance value corresponding to the predefined classes.

5. The method of claim 4, wherein the plurality of distance values of the plurality of predefined classes do not overlap.

6. The method of claim 4, wherein the plurality of distance values of the plurality of predefined classes are each configured based on a scan resolution.

7. The method of claim 1, wherein the deep neural network is trained based on a training dataset comprising a plurality of labelled images, each labelled image being labelled with one of the plurality of predefined classes which the labelled image belongs to.

8. The method of claim 7, each labelled image being a labelled difference image formed based on two 2D ultrasound images extracted at a predefined distance apart from a 3D ultrasound image volume acquired by a 3D ultrasound transducer, the predefined distance apart corresponding to one of the plurality of predefined classes.

9. The method of claim 1, further comprising:
for a respective pair of consecutive 2D ultrasound images of the series of 2D ultrasound images:
generating a difference image from the respective pair of consecutive 2D ultrasound images;
estimating, using the deep neural network, an estimated distance between the positions associated with the respective pair of consecutive 2D ultrasound images based on the classification of the difference image.

10. The method of claim 1, wherein the measurement of tissue is a measurement of tissue volume.

11. The method of claim 1, further comprising extracting diagnostic information from the modified series of 2D ultrasound images.

12. The method of claim 11, wherein the extracted diagnostic information is associated with one or more of the group consisting of: a hip-bone, an elbow, a carotid artery, a heart, one or more lung(s), a stomach, a liver, and one or more kidney(s).

13. The method of claim 1, further comprising:

extracting one or more features from the modified series of 2D ultrasound images, the one or more features associated with one or more of the group consisting of: a hip-bone, an elbow, a carotid artery, a heart, one or more lung(s), a stomach, a liver, and one or more kidney(s).

14. A system for generating a three-dimensional (3D) ultrasound image of a tissue volume, the system comprising:

an ultrasound transducer;

a memory; and at least one processor communicatively coupled to the memory and the ultrasound transducer, and configured to perform a set of operations, comprising:

generating a series of two-dimensional (2D) ultrasound images of a tissue volume associated with a plurality of positions, respectively, along a scanning direction of the tissue volume;

for a pair of consecutive 2D ultrasound images of the series of 2D ultrasound images, using a deep neural network to classify a difference between the pair of consecutive 2D ultrasound images of the series of 2D ultrasound images, wherein the deep neural network is trained to classify differences between images based on one of a plurality of predefined classes;

modifying a number of 2D ultrasound images in the series of 2D ultrasound images based on the classification of the difference between the pair of consecutive 2D ultrasound images of the series of 2D ultrasound images, thereby producing a modified series of 2D ultrasound images; and performing a measurement of tissue using at least one of the modified series of 2D ultrasound images.

15. The system of claim 14, wherein the set of operations further comprises rendering a 3D ultrasound image of the tissue based on the modified series of 2D ultrasound images.

16. The system of claim 15, wherein the tissue is rendered on a portable computing system.

17. The system of claim 14, wherein the plurality of predefined classes correspond to a plurality of distance values, respectively, and the set of operations further comprises estimating a distance value corresponding to the predefined classes.

18. The system of claim 17, wherein the plurality of distance values of the plurality of predefined classes do not overlap.

19. The system of claim 17, wherein the plurality of distance values of the plurality of predefined classes are each configured based on a scan resolution.

20. A computer program product, embodied in one or more non-transitory computer-readable storage mediums, comprising instructions executable by at least one processor to perform a method for generating a three-dimensional (3D) ultrasound image of a tissue volume, the method comprising:

generating a series of two-dimensional (2D) ultrasound images of a tissue volume associated with a plurality of positions, respectively, along a scanning direction of the tissue volume;

for a pair of consecutive 2D ultrasound images of the series of 2D ultrasound images, using a deep neural network to classify a difference between the pair of consecutive 2D ultrasound images of the series of 2D ultrasound images, wherein the deep neural network is trained to classify differences between images based on one of a plurality of predefined classes;

modifying a number of 2D ultrasound images in the series of 2D ultrasound images based on the classification of the difference between the pair of consecutive 2D ultrasound images of the series of 2D ultrasound images, thereby producing a modified series of 2D ultrasound images; and performing a measurement of tissue using at least one of the modified series of 2D ultrasound images.

* * * * *